United States Patent
Nishida et al.

(10) Patent No.: US 12,365,950 B2
(45) Date of Patent: Jul. 22, 2025

(54) METHOD OF DETECTING CONJUNCTIVAL DISEASE USING OCULAR SURFACE TISSUE, AND AGING BIOMARKER

(71) Applicants: OSAKA UNIVERSITY, Suita (JP); OTSUKA PHARMACEUTICAL CO., LTD., Tokyo (JP)

(72) Inventors: Kohji Nishida, Osaka (JP); Noriyasu Hashida, Osaka (JP); Tetsuya Iida, Osaka (JP); Shota Nakamura, Osaka (JP); Daisuke Motooka, Osaka (JP); Kazunobu Asao, Osaka (JP); Satoru Ando, Osaka (JP)

(73) Assignees: Osaka University, Osaka (JP); Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 17/252,982

(22) PCT Filed: Jun. 28, 2019

(86) PCT No.: PCT/JP2019/025827
§ 371 (c)(1),
(2) Date: Dec. 16, 2020

(87) PCT Pub. No.: WO2020/004626
PCT Pub. Date: Jan. 2, 2020

(65) Prior Publication Data
US 2021/0214775 A1 Jul. 15, 2021

(30) Foreign Application Priority Data
Jun. 29, 2018 (JP) .................................. 2018-124504

(51) Int. Cl.
C12Q 1/689 (2018.01)
C12Q 1/06 (2006.01)

(52) U.S. Cl.
CPC ............... *C12Q 1/689* (2013.01); *C12Q 1/06* (2013.01)

(58) Field of Classification Search
CPC .................................................... C12Q 1/689
See application file for complete search history.

(56) References Cited

U.S. PATENT DOCUMENTS

| 2014/0037688 A1 | 2/2014 | Berkes et al. |
| 2015/0259728 A1 | 9/2015 | Cutliffe et al. |

(Continued)

FOREIGN PATENT DOCUMENTS

| JP | 2015-188379 | 11/2015 |
| JP | 2016-525355 | 8/2016 |

(Continued)

OTHER PUBLICATIONS

Rubio, E.F. Eye 20:447-454. (Year: 2006).*

(Continued)

*Primary Examiner* — Diana B Johannsen
(74) *Attorney, Agent, or Firm* — HSML P.C.

(57) ABSTRACT

A method for detecting conjunctival diseases such as conjunctival MALT lymphoma, and an aging biomarker that serves as an indicator of the aging state of a subject are provided. The method for detecting conjunctival diseases comprises a step of comparing a microbial community structure of a microbiota in an ocular surface tissue specimen sampled from a healthy person with a microbial community structure of a microbiota in an ocular surface tissue specimen sampled from a subject to determine that the ocular surface tissue specimen of the subject has an indication of the conjunctival diseases. The aging biomarker a comprises bacterial species which belongs to the Coryne- (Continued)

bacteriaceae family or the Propionibacteriales family in an ocular surface tissue.

8 Claims, 14 Drawing Sheets

Specification includes a Sequence Listing.

(56)  References Cited

U.S. PATENT DOCUMENTS

| | | |
|---|---|---|
| 2018/0208982 A1 | 7/2018 | Komata et al. |
| 2020/0270686 A1 | 8/2020 | Nishida et al. |

FOREIGN PATENT DOCUMENTS

| | | |
|---|---|---|
| JP | 2017/014256 | 1/2017 |
| JP | 2017-029133 | 2/2017 |
| JP | 2017-029174 | 2/2017 |
| WO | 2012/118535 | 9/2012 |
| WO | 2017/170571 | 10/2017 |

OTHER PUBLICATIONS

Sohn, K. et al. The Brazilian Journal of Infectious Diseases 19(4):449-450. Jun. 2015 (Year: 2015).*
Wiley, L. et al. Investigative Ophthalmology & Visual Science 53(7):3896. Jun. 2012. (Year: 2012).*
Lu, L.J. and Liu, J. Yale Journal of Biology and Medicine 89:325. (Year: 2016).*
Dong, Q. et al., Supplementary Materials of Investigative Ophthalmology & Visual Science, 52(8):5408 (11 pages). (Year: 2011).*
Verma, V. et al. Survey of Ophthalmology 53(4):312. (Year: 2008).*
Graham, et al., Ocular Pathogen or Commensal: A PCR-Based Study of Surface Bacterial Flora in Normal and Dry Eyes, Investigative Opthalmology & Visual Science, vol. 48, No. 12, Dec. 1, 2007, pp. 5616-5623.
Thiel, et al., "Normal Flora of the Human Conjunctiva: A Study of 135 Persons of Various Ages", Klin Monbl Augenheilkd, vol. 205, No. 12, Dec. 1, 1994, pp. 348-357—Abstract.
Collina, et al., "Chlamydia psittaci in ocular adnexa MALT lymphoma: a possible role in lymphomagenesis and a different geographical distribution", Infectious Agents and Cancer, Biomed Central Ltd, vol. 7, No. 1, 2012, 11 pages.
Dong, et al., "Diversity of Bacteria at Healthy Human Conjunctiva", Investigative Opthalmology & Visual Science, vol. 52, No. 8, Jul. 20, 2011, pp. 5408-5413.
Extended European Search Report issued in corresponding European Patent Application No. 19825086.2, Feb. 14, 2022, 12 pages.
English Translation of the International Preliminary Report on Patentability and Written Opinion issued in International Application No. PCT/JP2019/025827, Dec. 29, 2020, 25 pages.
International Search Report issued in International Application No. PCT/JP2019/025827, Oct. 1, 2019, 4 pages with translation.
Written Opinion of the International Search Authority issued in International Application No. PCT/JP2019/025827, Oct. 1, 2019, 9 pages.
Zhou, et al., "The conjunctival microbiome in health and trachomatous disease: a case control study", Genome Medicine, 2014, vol. 6, article No. 99, 10 pages.
Aoki, et al., "Indentification of Causative Pathogens in Eyes with Bacterial Conjunctivitis by Bacterial Cell Count and Microbiota Analysis", Ophthalmology, 2013, vol. 120, No. 4, pp. 668-676.
Shibagaki, et al., "Aging-related changes in the diversity of women's skin microbiomes associated with oral bacteria", Scientific Reports, 2017, vol. 7, article No. 10567, pp. 1-10.
Asao, et al., "Conjuncti val dysbiosis in mucosa-associated lymphoid tissue lymphome", Scientific Reports, 2019, vol. 9, article No. 8424, pp. 1-10.
Juge, et al., "Shift in skin microbiota of Western European women across aging", Journal of Applied Microbiology, Sep. 2018, vol. 125, No. 3, pp. 907-916.
Notice of Reasons for Refusal issued in corresponding Japanese Patent Application No. 2023-111475, Jun. 18, 2024, 13 pages w/translation.

* cited by examiner

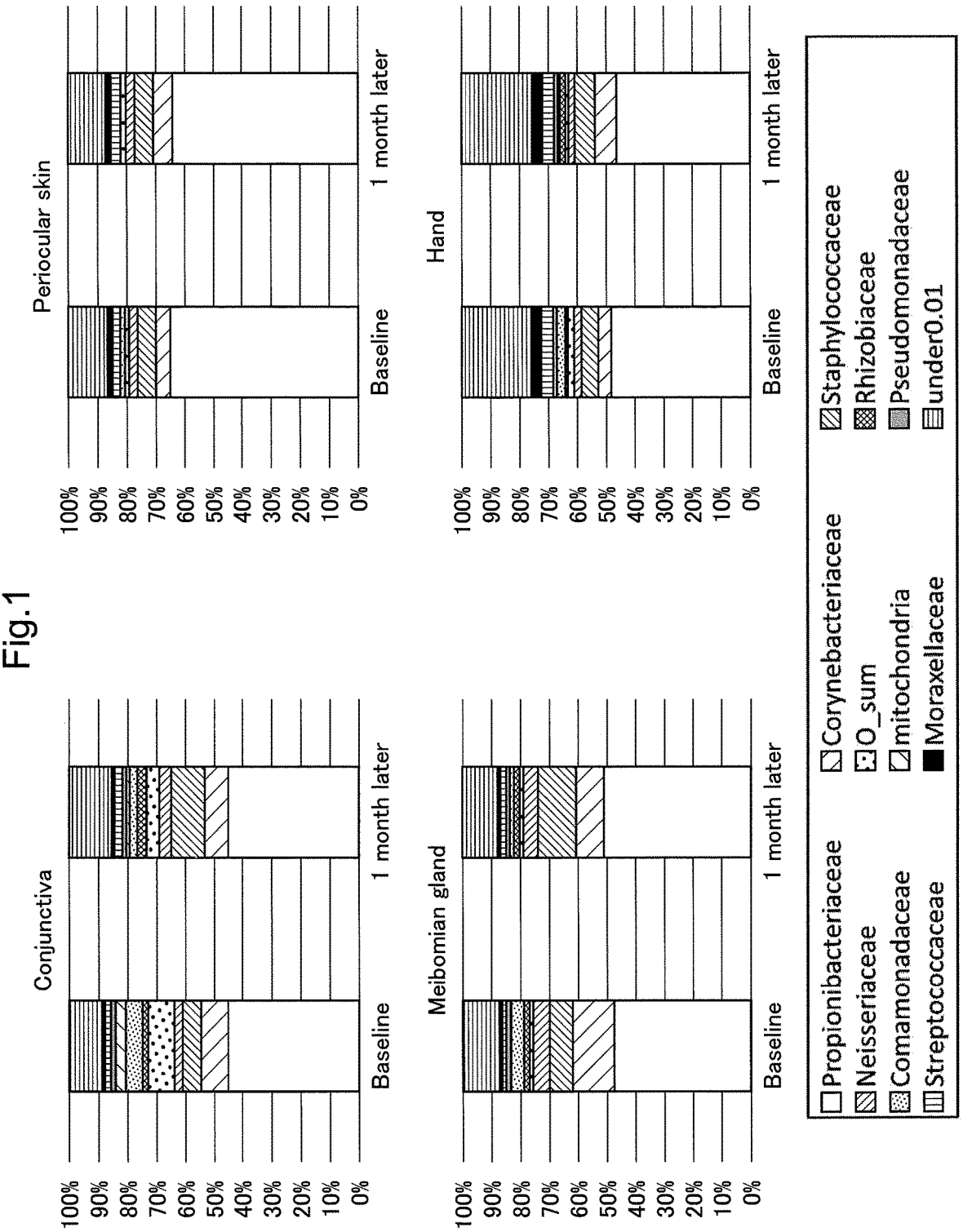

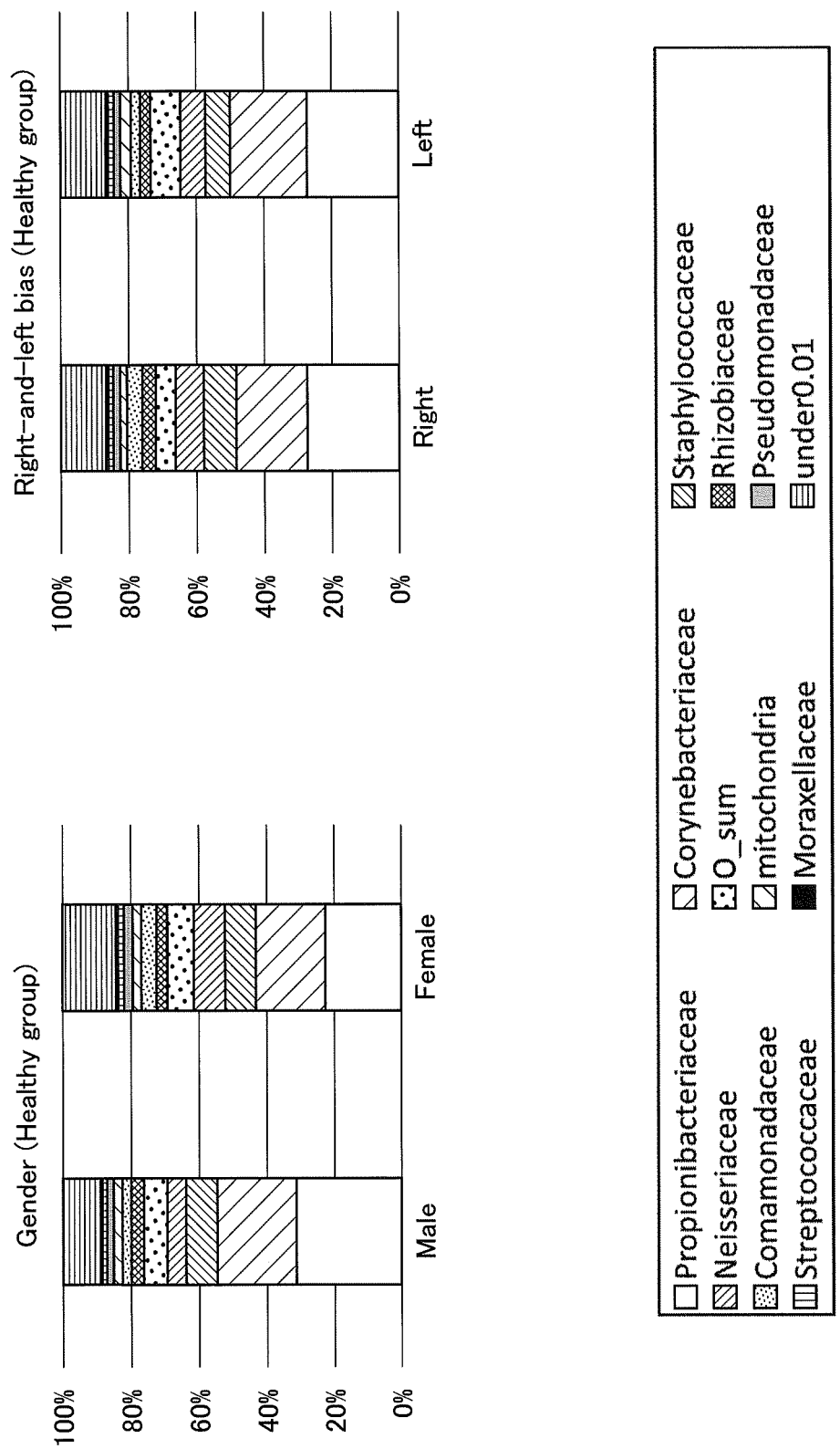

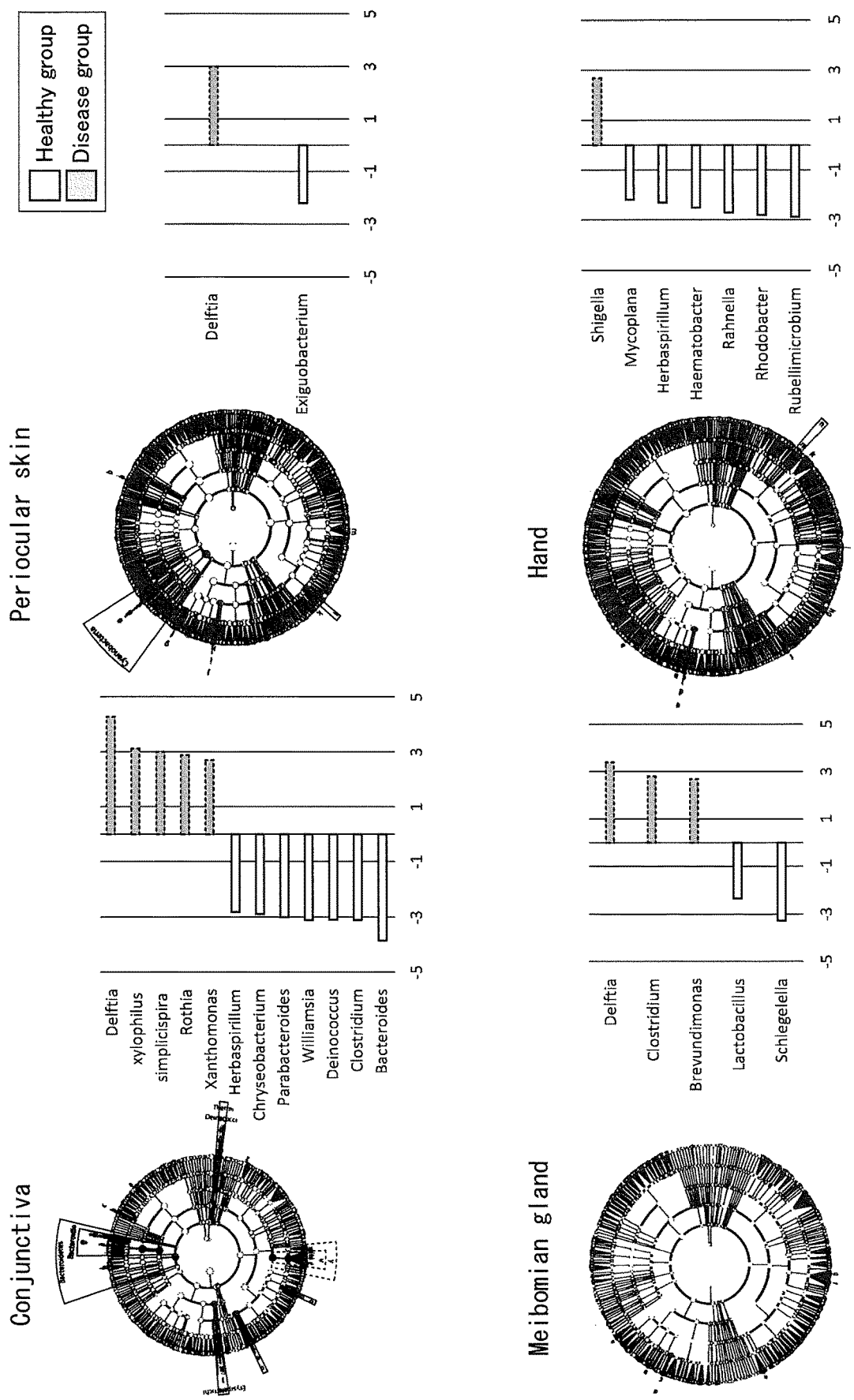

```
                         SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
agrgtttgat cmtggctcag                                              20

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
tgctgcctcc cgtaggagt                                               19

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
cttggtcatt tagaggaagt aa                                           22

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gcatcgatga agaacgcagc                                              20
```

METHOD OF DETECTING CONJUNCTIVAL DISEASE USING OCULAR SURFACE TISSUE, AND AGING BIOMARKER

TECHNICAL FILED

The present invention relates to a method of detecting a conjunctival disease using an ocular surface tissue, and an aging biomarker.

BACKGROUND ART

Factors which quantitatively vary in correlation to states of living bodies or specific diseases are referred to as biomarkers, and serve as indicators for quantitatively recognizing biological changes in living bodies such as aging and diseases. Biomarkers which quantitatively vary in correlation to age and allow to predict aging are referred to as aging biomarkers. Biomarkers which quantitatively vary in correlation to specific diseases and can contribute to diagnosis of the diseases and to establishment of effective therapies are referred to as disease biomarkers. Particularly, in a current situation facing super-aged society, measures which allow to grasp health states of elderly people and to extend health life expectancy are being taken in an active manner. However, there are few means, including aging biomarkers, for evaluating health states and aging states in an objective and highly reproducible manner. In a current situation, there is a state of limited way in which aging-related-changes specific to elderly people are checked with blood tests, diagnostic imaging or the like. For example, it has been reported that estrogen, testosterone, insulin-like growth factor-1, Vitamin D and the like in blood components quantitatively vary in correlation to age. Also, it is known that incidence of diseases such as lifestyle-related disease and stroke increases along with aging.

In recent years, transcriptome/meta-transcriptome analysis which is an exhaustive gene expression analysis, metabolome analysis which is an exhaustive metabolite analysis, metagenomic analysis which is an exhaustive genome sequence analysis using next-generation sequencer, and the like are performed. Attempts are being made to utilize the technology in exhaustive search for new biomarkers. For example, it has been reported that health states and aging states of subjects can be inferred from abundance ratios of indigenous bacteria of skin surface, especially *Propionibacterium acnes* (occasionally abbreviated as "*P. acnes*" in the followings), and the like by using an exhaustive genome analysis using a next-generation sequencer (refer to Patent Literature 1). However, it has been also reported that an abundance of *P. acnes* on the skin surface depends on physical conditions such as degree of skin oiliness, acne, thinning hair, hair loss, and menopause, other than age. Therefore, there is still a demand for search for aging biomarkers with which health states and aging states can be evaluated in an objective and highly reproducible manner.

Disease biomarkers can contribute to diagnosis of specific diseases and to establishment of effective therapies. For example, there is a demand for search for disease biomarkers which allow to clarify a pathogenic mechanism and to predict an onset in diseases in which incidence increases in association with aging, such as conjunctival mucosa-associated lymphoid tissue (abbreviated as "MALT" in the followings) lymphoma, age-related macular degeneration, cataract, and glaucoma in an ophthalmic field.

Here, conjunctival MALT lymphoma is known as localized tumor of low malignant potential, and extranodal marginal zone B-cell lymphoma of MALT type is the most typical histological subtype. It has been estimated that lymphoma in the ocular accessory gland has a frequency of approximately 8% of extranodal lymphoma. It has been reported that a prognosis of primary conjunctival lymphoma is favorable with long-term survival expected among patients with primary lymphoma. Histologically, conjunctival MALT lymphoma has characteristics similar to gastric MALT lymphoma and is thought to result from a chronic inflammatory response. *Helicobacter pylori* DNA has been detected in some cases of conjunctival MALT lymphoma, and *Chlamydia psittaci* has been reported to be involved in its onset, suggesting that these bacterial species may be the causative pathogens. However, in a current situation, the pathophysiology of conjunctival MALT lymphoma has not been completely elucidated.

In living organisms, it is known that a wide variety of indigenous microbes regulate and control homeostasis, and that microbiotas which exist in the oral cavity, intestinal tract, respiratory tract, anus, skin, and the like play an important role in maintaining health, onset and progression of diseases, and the like. In particular, in the human intestinal tract, more than 1000 kinds of intestinal microbes form their own stable environment as intestinal microbiota, and are involved in maintaining homeostasis of living organisms. It has been discussed that such a change in balance of the microbiota of living organisms causes abnormal homeostasis and may be involved in the onset and progression of diseases. For example, it has been reported that dysbiosis which is an imbalance in a microbiota induces systemic diseases such as inflammatory bowel disease, obesity, and cardiovascular disease. In addition, a relationship between the immune system and the indigenous microbiota of living organisms in biological defense and tissue repair has also been reported. Pathological changes in microbiotas of *Staphylococcus epidermidis* which is a skin indigenous bacterium, and the like, have been shown to cause opportunistic infections such as onset of catheter infection, endocarditis of artificial valves and endophthalmitis. Furthermore, an association between dysbiosis and central nervous system disorders such as autism, multiple sclerosis, anxiety-depressive behavior, and functional gastrointestinal disorders has been reported at a clinical level, and a treatment in which the microbiota of these symptoms is targeted has also been suggested. As described above, the change in the microbiota causes various symptoms such as infection of pathogens or inflammation to living organisms, and may cause living organisms to fall into a fatal state.

Conjunctiva-associated lymphoid tissue (CALT), a biological defense mechanism, exists on an ocular surface. It is known that the ocular surface is continuously exposed to external environments such as temperature changes, ultraviolet light and oxidative stress, and these stresses are involved in the onsets of pterygium, dry eye, corneal dystrophy, Fuchs corneal endothelial dystrophy, and the like. This suggests that a change in a microenvironment on the ocular surface may cause a change in a microbiota, which may lead to the onset of diseases.

Based on such a correlation between a microbiota and the onset of specific diseases, there is a possibility that the onset and progression of diseases can be predicted by grasping changes in the microbiota due to the diseases as biomarkers. However, it is not clear whether stable microbiota such as intestinal microbiota exists in ocular surface tissues. Furthermore, findings on a relevance to specific diseases have not been sufficiently obtained in a current situation.

CITATION LIST

Patent Literature

[Patent Literature 1] Japanese Unexamined Patent Application Publication No. 2017-29133

SUMMARY OF INVENTION

Technical Problem

As described above, conventionally, a technology for evaluating an aging state in an objective and highly reproducible manner has been reported only at a research level, and there is still a demand for establishment of the technology. Fundamentally, defining "aging" is difficult, and it is desired to evaluate not only aging based on normal calendar age but also an overall picture of aging, including a pathological aging state that may lead to the onset of future diseases or the like, in an objective and highly reproducible manner. In particular, assessing the aging state, and the onset and progression of various diseases with quantitative properties can be applied to a prevention of the onset of diseases and a selection of effective treatment methods, which leads to reduction of healthcare costs and is also useful for socioeconomy.

Therefore, the present invention aims to construct a technology in which the onset or progression of an aging state or a specific disease can be evaluated in an objective and highly reproducible manner, and in particular, to provide a method of detecting conjunctival diseases such as conjunctival MALT lymphoma, and to provide an aging biomarker that serves as an indicator of the aging state.

Solution to Problem

The present inventors have conducted further studies to solve the above problem, and as a result, a finding has been obtained that dysbiosis of a conjunctival microbiota may cause immunological changes in the conjunctival mucosa and may be involved in the onset of conjunctival MALT lymphoma. Subsequently, as a result of investigating microbial community structures of microbiotas of ocular surface tissues in persons suffering from conjunctival MALT lymphoma and that of healthy persons, a change in the microbial community structure specific to the persons suffering from conjunctival MALT lymphoma has been found, and a finding that the onset and progression of conjunctival MALT lymphoma can be detected based on such a change in the microbial community structure has been obtained. In addition, a finding that a change in the microbial community structure of the microbiota of the ocular surface tissue can be used as an indicator of the aging state has been obtained. The present inventors have achieved the present invention based on these findings.

That is, the following inventions [1] to [9] are provided.

[1] A method of detecting a conjunctival disease using an ocular surface tissue, the method comprising a step of comparing a microbial community structure of a microbiota included in an ocular surface tissue specimen sampled from a healthy person, with a microbial community structure of a microbiota included in an ocular surface tissue specimen sampled from a subject to detect an ocular surface tissue specimen which is sampled from the subject evaluated as having the conjunctival disease based on a change in the microbial community structure between the healthy person and the subject.

According to the above configuration [1], there is provided a method in which the onset, onset risk, degree of progression and the like of a conjunctival disease can be detected in an objective and highly reproducible manner based on a change in the balance of the microbiota existing in the ocular surface tissue. Conventionally, it has not been clear whether a microbiota such as the intestinal microbiota exists stably in ocular surface tissues including the conjunctiva, and it has been much less clear whether a specific microbiota is involved in conjunctival diseases. However, the present inventors have clarified a relationship between a change in balance of the microbiota existing in the ocular surface tissue and conjunctival diseases. Therefore, according to this configuration, it is possible to quantitatively evaluate the onset and progression degree of conjunctival disease, including an initial stage without subjective symptoms. This can be applied to prevention of the onset of the diseases and selection of an effective treatment method, which leads to a reduction in medical costs and is also useful from a socioeconomic viewpoint. According to this configuration, since ocular surface tissue specimens are used, specimens can be sampled more easily than those obtained by blood collection or the like. In addition, there is an advantage that it is non-invasive and has a low mental and physical burden.

[2] The method according to [1], wherein the conjunctival disease is conjunctival mucosa-associated lymphoid tissue lymphoma.

According to the above configuration [2], there is provided a method in which the onset, onset risk, degree of progression and the like of conjunctival mucosa-associated lymphoid tissue lymphoma can be detected in an objective and highly reproducible manner based on a change in the balance of the microbiota existing in the ocular surface tissue.

[3] The method according to [2], wherein the change in the microbial community structure is a change in an abundance or an abundance ratio of a bacterial species which belongs to at least one genus selected from *Delftia* genus, *Xylophilus* genus, *Simplicispira* genus, *Rothia* genus, *Xanthomonas* genus, *Bacteroides* genus, *Clostridium* genus, *Deinococcus* genus, *Williamsia* genus, *Parabacteroides* genus, *Chryseobacterium* genus, *Herbaspirillum* genus, *Brevundimonas* genus, *Lactobacillus* genus, *Schlegelella* genus, and *Exiguobacterium* genus.

According to the above configuration [3], it has been confirmed that the abundance or the abundance ratio of the bacterial species changes due to the onset of the conjunctival mucosa-associated lymphoid tissue lymphoma or the like. There is provided a method in which the onset, risk of onset, and degree of progression of conjunctival mucosa-associated lymphoid tissue lymphoma and the like can be detected based on the change in the abundance or the abundance ratio of such a bacterial species in a more objective and highly reproducible manner.

[4] The method according to [3], wherein the change in the microbial community structure is a change in the abundance or the abundance ratio of the bacterial species which belongs to the *Delftia* genus, and an increase in the abundance or the abundance ratio of the bacterial species which belongs to the *Delftia* genus is evaluated as the conjunctival disease.

According to the above configuration [4], it has been confirmed that the abundance or the abundance ratio of the bacterial species which belongs to the *Delftia* genus increases due to the onset of conjunctival mucosa-associated lymphoid tissue lymphoma or the like. There is provided a method in which the onset, risk of onset, and degree of progression of conjunctival mucosa-associated lymphoid tissue lymphoma, and the like can be detected based on the increase in the abundance or the abundance ratio of such a bacterial species in a more objective and highly reproducible manner.

[5] The method according to [3] or [4], wherein the change in the microbial community structure is a change in the abundance or the abundance ratio of the bacterial species which belongs to at least one genus selected from the *Bacteroides* genus and the *Clostridium* genus in a conjunctiva, and a decrease in the abundance or the abundance ratio of the bacterial species which belongs to at least one genus selected from the *Bacteroides* genus and the *Clostridium* genus is evaluated as the conjunctival disease.

According to the above configuration [5], it has been confirmed that the abundance or the abundance ratio of the bacterial species which belongs to the *Clostridium* genus decreases in the conjunctiva due to the onset of the conjunctival mucosa-associated lymphoid tissue lymphoma or the like. There is provided a method in which the onset, risk of onset, and degree of progression of conjunctival mucosa-associated lymphoid tissue lymphoma, and the like can be detected based on such a decrease in the abundance or the abundance ratio of the bacterial species in a more objective and highly reproducible manner.

[6] The method according to any of the above [1] to [5], wherein the change in the microbial community structure determines a base sequence of a 16S rRNA gene of a microbe constituting the microbiota, and is evaluated based on the base sequence.

According to the configuration of [6], there is provided a method in which the onset and progression of a conjunctival disease, and the like can be detected in an objective and highly reproducible manner based on the change in the balance of the microbiota existing in the ocular surface tissue, by performing a 16S rRNA gene analysis. According to this configuration, it is possible to exhaustively analyze microbial species existing in the ocular surface tissue by metagenomic analysis using a next-generation sequencer or the like without passing through a stage of isolation culture, and to analyze the microbiota in the ocular surface tissue with accuracy and high reliability. In other words, it is possible to exhaustively analyze the microbial community structure of the microbiota without bias to specific microbial species, including hardly culturable microbial species that has been difficult to detect by analyses based on conventional culture methods, and accuracy and reliability of analysis results are improved. With this, there is provided a method in which the onset, risk of onset, and degree of progression of conjunctival mucosa-associated lymphoid tissue lymphoma, and the like can be detected more accurately and reliably.

[7] An aging biomarker for detecting an aging state, the aging biomarker comprising a bacterial species which belongs to at least one family selected from Corynebacteriaceae family and Propionibacteriales family in an ocular surface tissue. According to the configuration [7], there is provided an aging biomarker that can evaluate an aging state with bacteria belonging to Corynebacteriaceae family and Propionibacteriales family existing in the ocular surface tissue. According to this configuration, the aging state of the subject can be detected in an objective and highly reproducible manner, and the aging state of the whole body can be detected from a specimen sampled from a local part of the eye. Conventionally, it is not clear whether a microbiota such as the intestinal microbiota exists stably in ocular surface tissues including the conjunctiva, and it is much less clear whether a specific microbiota is involved in conjunctival diseases. However, the present inventors have clarified a relationship between a change in a balance of the microbiota existing in the ocular surface tissue and the aging state, and furthermore, a relationship to the onset of the specific disease. Therefore, the biomarker of this configuration can be used not only for detecting an aging state but also for detecting a disease state that develops in association with aging, and can be used for elucidating the cause of a systemic disease resulting from an aging-related change. That is, the present invention can be used to quantitatively evaluate the onset, onset risk, progression degree and the like of diseases, including not only the aging state but also the initial stage without subjective symptoms. With this, the biomarker of this configuration can be applied to prevention of the onset of diseases and selection of an effective treatment method, which leads to a reduction in medical costs and is also useful from a socioeconomic viewpoint.

[8] The aging biomarker according to [7], wherein the aging biomarker comprises a 16S rRNA gene of the bacterial species.

According to the configuration of the above [8], by performing 16S rRNA gene analysis, the aging biomarker capable of detecting the aging state in an objective and highly reproducible manner based on the change in the balance of the microbiota existing in the ocular surface tissue is provided. The 16S rRNA gene can be analyzed by metagenomic analysis using a next-generation sequencer or the like. According to such an analysis, it is possible to exhaustively analyze the microbial species existing in the ocular surface tissue without passing through a stage of isolation culture, and to analyze the microbiota in the ocular surface tissue with accuracy and high reliability. In other words, it is possible to exhaustively analyze the microbial community structure of the microbiota without bias to specific microbial species, including hardly culturable microbial species that has been difficult to detect by analyses based on conventional culture methods, and accuracy and reliability of analysis results are improved. Therefore, according to the aging biomarker of this configuration, the aging state can be detected more accurately and reliably, and in an objective and highly reproducible manner.

[9] The aging biomarker according to [7] or [8], wherein the aging state is a physiological aging state or a pathological aging state.

According to the configuration of the above [9], there is provided an aging biomarker in which not only a physiological aged state (pre-symptomatic state) based on calendar age but also a pathological aging state that causes a pathological state due to abnormally accelerated aging or the like can be detected. Therefore, the biomarker of this configuration can be used not only for detecting the aging state but also for detecting the disease state that develops in association with aging, and can be used for elucidating the cause of a systemic disease resulting from an aging-related change.

BRIEF DESCRIPTION OF DRAWINGS

FIG. 1 is graphs showing results of verifying a stability of bacterial compositions among 4 sites (conjunctiva, meibomian gland, periocular skin, and hand) from which specimens were sampled.

FIG. 2A is graphs showing results of verifying an influence by gender and right-and-left bias in microbial community structures of conjunctival microbiotas, and showing results of a healthy group.

FIG. 5 is a figure which shows results of verifying differences in bacterial compositions of microbiotas among 4 sites (conjunctiva, meibomian gland, periocular skin, and hand) from which specimens were sampled, and is bar graphs showing LDA scores and phylogenetic diagrams showing plots of the LDA scores.

DESCRIPTION OF EMBODIMENTS

Figure 2B:
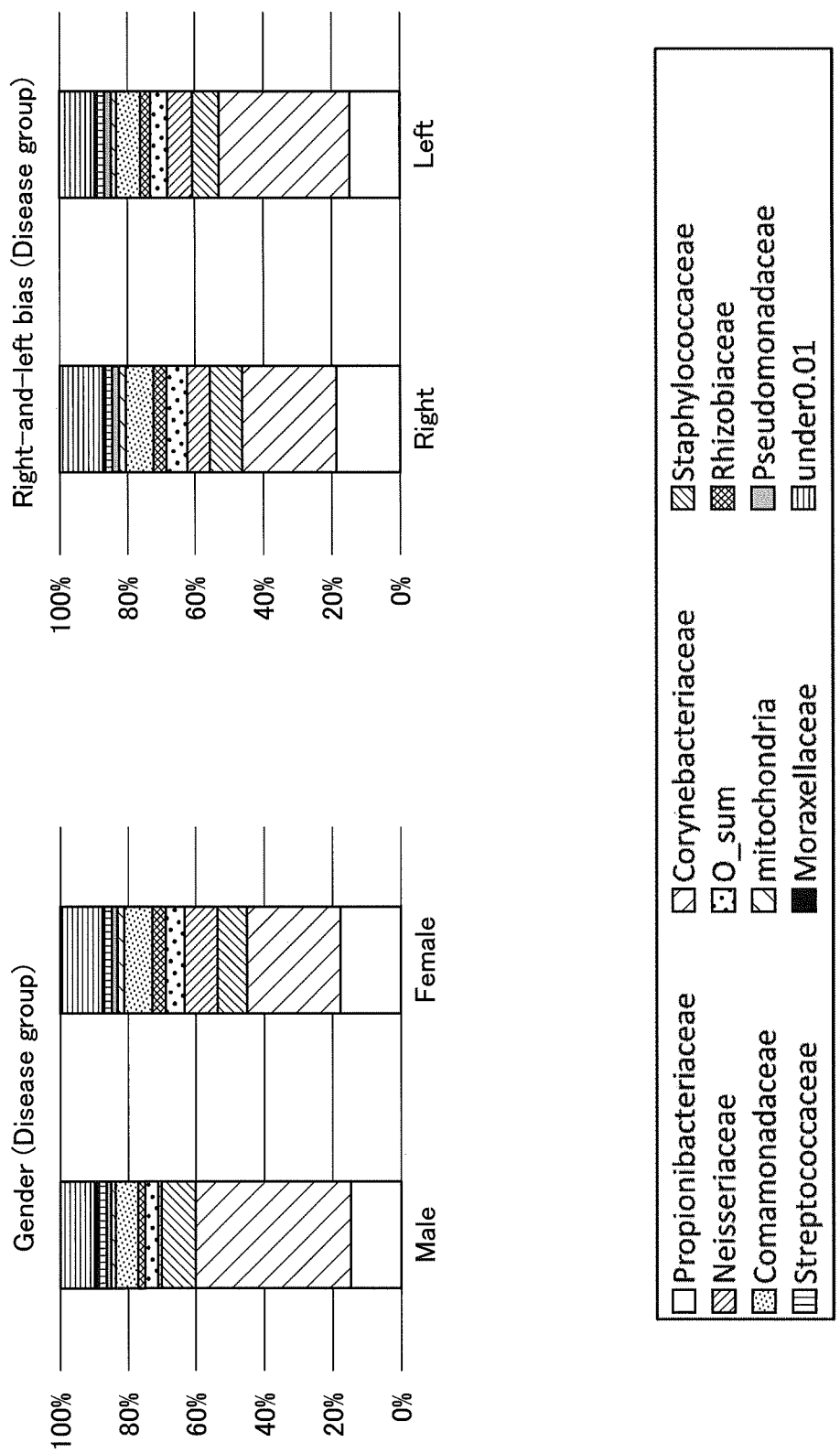
FIG. 2B is graphs showing results of verifying an influence by gender and right-and-left bias in microbial community structures of conjunctival microbiotas, and showing results of a disease group.

Hereinafter, a method of detecting a conjunctival disease using an ocular surface tissue and an aging biomarker according to an embodiment of the present invention will be described in detail. However, the present invention is not limited to the embodiment described below.

[Method of Detecting Conjunctival Disease]

The method of detecting a conjunctival disease according to the present embodiment provides information on a pathological state of a conjunctival disease based on a change in a balance of a microbiota existing in an ocular surface tissue. That is, the method of detecting a conjunctival disease according to the present embodiment is based on a finding that a change in a microbial community structure of a microbiota existing in the ocular surface tissue is correlated with a pathology of a conjunctival disease.

The conjunctival disease to be detected by the method of detecting a conjunctival disease according to the present embodiment generally means diseases that cause conjunctival abnormalities. In particular, diseases that cause abnormalities in the conjunctiva as a result of aging-related changes and in which incidence increases with aging are included. For example, conjunctival MALT lymphoma, pterygium, dry eye, conjunctival relaxation, glaucoma, age-related macular degeneration (AMD), and the like are exemplified.

In the method of detecting a conjunctival disease according to the present embodiment, the onset, progression degree and the like of a conjunctival disease are detected based on a change in a microbial community structure of a microbiota contained in an ocular surface tissue specimen derived from a subject. That is, it is possible to detect the ocular surface specimen sampled from the subject who has been evaluated as having the conjunctival disease based on the change in the microbial community structure of the microbiota, which allows to detect whether the subject has developed the conjunctival disease and whether there is a risk of developing the conjunctival disease in the future.

Ocular surface tissues include a tissue on a surface of an eyeball, an appendage which is a structure close to a surface of the eyeball, and the like. The eyeball is protected by an eyelid, eyelashes at upper and lower edges of the eyelid and the like, and an outer membrane thereof is constituted by a cornea and a sclera. The sclera from the inside of the eyelid to the front of the eyeball is covered with a conjunctiva, and a Tenon's capsule is located between the conjunctiva and the sclera. The conjunctiva includes an eyelid conjunctiva that covers the inside of the eyelid, an eyeball conjunctiva that covers a part of the front surface of the eyeball, a fornix conjunctiva that is a transition part between the two, and the like. In addition, a meibomian gland opens at a margin of the eyelid, a lacrimal gland opens on an ear side of a superior conjunctival fornix, and an accessory lacrimal gland opens at the superior and inferior conjunctival fornix. Examples of the ocular surface tissue include those described above, but are not limited thereto. In addition, the ocular surface tissue includes secretions and the like from the ocular surface tissue described above, and includes, for example, a tear film or eye oil composed of an oil layer and a liquid layer (a mucin layer and an aqueous layer), leakage/exudate from blood vessels and the like, cells/tissue fragments such as detached epithelial cells and others.

Collection of ocular surface tissue specimens can be performed using a technique known in the art as long as bacteria existing in the ocular surface tissue can be sampled. For example, rubbing an ocular surface tissue in an aseptic condition with a swab (cotton swab) or a spatula (ocular surface tissue scraping specimen), and collecting secretions such as leakage and exudate from the ocular surface tissue (ocular surface tissue secretion specimen) enable to perform the collection. In addition, when the ocular surface tissue is sampled, a local anesthesia or the like may be given as needed. The obtained ocular surface tissue specimen can be dissolved or suspended in an appropriate liquid as needed. The amount of the ocular surface tissue specimen to be sampled is not particularly limited, but may be, for example, an amount obtained by rubbing with 1 swab. Thus, the ocular surface tissue specimen can be sampled by simple and non-invasive methods such as rubbing ocular surface tissues.

In the method of detecting a conjunctival disease according to the present embodiment, a change in the microbiota existing in the ocular surface tissue can be determined using a known technique in the art. For example, microbiota analysis methods targeting a 16S rRNA gene, and the like can be used. Microbiota analysis methods include metagenome analysis method, Terminal Restriction Fragment Length Polymorphism (T-RFLP), Denaturing Gradient Gel Electrophoresis (DGGE), Temperature Gradient Gel Electrophoresis (TGGE) and fluorescence in situ hybridization (FISH)-flow cytometry (FISH-FCM), but are not limited thereto. In particular, a metagenome analysis method using a next-generation sequencer can be used.

When the metagenome analysis method is used, a base sequence of 16S rRNA gene of, for example, microbes (in particular, bacteria) contained in an ocular surface tissue specimen of a subject is analyzed, and it is possible to detect an ocular surface specimen sampled from the subject who has been evaluated as having the conjunctival disease based on the obtained base sequence data. By using the next-generation sequencer, it becomes possible to identify the microbial species, its abundance ratio and the like while the microbiota which has been difficult to identify by conventional culture methods is made a single group. Therefore, since it is not necessary to go through a stage of isolation culture, exhaustive analysis of microbial species contained in the whole specimens sampled has become possible without bias to specific microbial species including hardly culturable microbial species that has been difficult to detect by analysis based on conventional culture methods. Furthermore, by checking against the existing database, the microbial species can be identified taxonomically, and characteristics of the microbial community structure can be analyzed.

In the analysis of the base sequence of the 16S rRNA gene, as a beginning, genomic DNA of a microbe contained in a specimen of ocular surface tissue of a subject is extracted. The method for extracting bacterial genomic DNA is not particularly limited, and it can be performed by using a known technique in the art. For example, heat extraction method, alkali heat extraction method, phenol/chloroform extraction method, or the like can be used. In addition, commercially available extraction kits such as PowerSoil (registered trademark) DNA Isolation Kit (MoBio, Carlsbad, CA) can be used.

Next, the base sequence of the 16S rRNA gene contained in the extracted genomic DNA is determined. The 16S rRNA gene may be sequenced in the entire region, but it is preferable to sequence a specific region as long as the sequence characteristics among each microbial species are reflected. Nine hypervariable regions called V1-V9 are adjacent to the 16S rRNA gene in a form locating predominantly in a region that is highly conserved across microbial species. By using such a hypervariable region as a target for base sequence determination, identification of microbial species can be performed. Therefore, it is preferable to determine a base sequence of any of the hypervariable regions or of a region including a plurality of the regions. For example, a region including V1-V2, a region including V3-V4, and the like can be given; however, it is not limited to such a region.

When determining a base sequence, the region for determining the base sequence may be amplified, if necessary, and the obtained nucleic acid amplified fragment (amplicon) can be used as a base sequence determination target. Amplification of nucleic acids can be performed using techniques known in the art. For example, polymerase chain reaction (PCR) and the like can be used. Primers used in the nucleic acid amplification reaction can be designed based on a known technique in the art. The primer is preferably designed so as to include a region which is relatively universally conserved in the bacterial 16S rRNA genes of the ocular surface tissue. For example, a universal primer for the 16S rRNA gene can be used. The primer may be designed so that a sequence required for base sequence determination is added to the amplified nucleic acid fragment. For example, a barcode sequence used for identification in samples, and the like are included.

When determining the base sequence, the amplified nucleic acid fragment may be previously purified by a technique known in the art. The base sequence can be determined using any of techniques known in the art. For example, it may be performed by a sequencer or the like based on the conventional Sanger method or the like, but from a viewpoint of ability to analyze the base sequence and the like, it is preferable to perform by a next-generation type sequencer or the like based on the Sequencing by Synthesis method, pyrosequencing method, ligase reaction sequencing method or the like. As the next-generation sequencer, for example, MiSeq (Illumina) or the like can be used, and sequence determination can be performed according to the manufacturer's protocol.

Since the obtained base sequence data (read) may contain low-quality reads due to incomplete sequencing reaction and the like, removing low-quality reads by read trimming may be performed if necessary. Trimming can be performed using, for example, BBtrim or the like.

Analyzing the microbiota is performed based on the determined base sequence. Analysis of the microbiota can be performed using any of techniques known in the art, and can be analyzed by visualizing or digitizing the microbial community structure of the microbiota, and for example, principal component analysis (PCA), principal coordinate analysis (PCoA) or the like can be used. Analysis of the microbiota can be performed using analysis software, a database, or the like known in the art. As an analysis software, for example, QIIME or the like can be used. As a database, for example, Greengenes, SILVA, NCBI, or the like can be used, and homology analysis, phylogenetic analysis, or the like is performed on the database.

In addition, the obtained base sequence data are classified into a plurality of clusters based on sequence similarity by OTU (Operational Taxonomic Unit) analysis, and the base sequence with the highest occurrence frequency in each OUT is set as a representative sequence. An analysis may be performed using such a representative sequence. At the time, the similarity of the base sequences for classification into the same cluster can be appropriately set based on the required reliability and the like. For example, 95% or more, 97% or more, and 99% or more can be set. As a software for OTU analysis, UCLUST, UPARSE, USEARCH, or the like can be used.

A conjunctival disease is detected by comparing the microbial community structure of the microbiota from the ocular surface tissue of the subject with that of healthy persons. Here, the microbes include bacteria or funguses, and bacteria are particularly preferable. For example, among bacteria constituting the microbiota derived from ocular surface tissues, the abundance or abundance ratio of bacteria belonging to a specific phylum, class, order, family, genus, or species can be used as an indicator. When it is determined that the abundance or the abundance ratio of the above of the subject is significantly increased or decreased as compared to that of healthy persons, it can be determined that there is a risk that the subject is suffering from a conjunctival disease or develops a conjunctival disease in the future. Here, the abundance ratio can be a ratio, a difference, a sum, or a product of the abundance ratios of a plurality of bacteria belonging to a specific phylum, class, order, family, genus, or species. At the time, a determination as to whether the abundance or abundance ratio of the above of the subject is significantly increased or decreased as compared to that of healthy persons can be performed by predetermining a reference value of the abundance or abundance ratio of bacteria belonging to a specific phylum, class, order, family, genus or species in the microbiota derived from the ocular surface tissue and by comparing it with the reference value. In addition, the determination may be performed based on statistical differences such as the abundance or abundance ratio of bacteria belonging to a specific phylum, class, order, family, genus, or species among the subjects. At the time, a determination of suffering from a conjunctival disease may be a determination at any level of bacterial phylum, class, order, family, genus, and species. Also, it may be a determination based on a level of 1 phylum, class, order, family, genus, or species, or may be a determination based on a level of a plurality of phyla, classes, orders, families, genera, or species.

A determination of conjunctival MALT lymphoma based on changes in the microbial community structure of, for example, an ocular surface tissue, particularly, a conjunctiva, can be performed on healthy persons using an increase in the abundance or abundance ratio of bacteria belonging to the following genus as an indicator. If the abundance or abundance ratio of the following bacteria increases more than that in healthy persons, it can be determined that the subject has developed conjunctival MALT lymphoma, or has a risk of developing conjunctival MALT lymphoma in the future.

*Delftia* genus bacteria (Proteobacteria phylum, Betaproteobacteria class, Burkholderiales order, Comamonadaceae family, *Delftia* genus)

*Xylophilus* genus bacteria (Proteobacteria phylum, Gamma Proteobacteria class, Xanthomonadales order, Xanthomonadaceae family, *Xylophilus* genus)

*Simplicispira* genus bacteria (Proteobacteria phylum, Betaproteobacteria class, Burkholderiales order, Comamomonadaceae family, *Simplicispira* genus)

*Rothia* genus bacteria (Actinobacteria phylum, Actinobacteria class, Micrococcales order, Micrococcaceae family, *Rothia* genus)

*Xanthomonas* genus bacteria (Proteobacteria phylum, Gammaproteobacteria class, Xanthomonadales order, Xanthomonadaceae family, *Xanthomonas* genus)

Particularly preferably, conjunctival MALT lymphoma can be determined using an increase in the abundance or abundance ratio of *Delftia* genus bacteria as an indicator. Here, *Delftia* genus bacteria are aerobic Gram-negative rods. *Delftia* genus bacteria exhibit resistance to β-lactam and aminoglycoside antibiotics. It is known that they adhere to contact lens cases and form biofilms, causing microbial and infiltrative keratitis to develop on the spherical surface of the eyeball. In addition, *Delftia* genus bacteria have an ability to oxidatively degrade and utilize glucose. This can cause changes in a conjunctival environment, and is known to be caused by changes in glucose levels in some corneal abnormalities, for example, abnormalities in the corneal epithelium. Therefore, *Delftia* genus bacteria may cause conjunctival MALT lymphoma as an aggressive factor by interfering with CALT by altering the state of the conjunctiva.

In addition, a determination of conjunctival MALT lymphoma based on changes in the microbial community structure of ocular surface tissues, particularly the conjunctiva can be performed on healthy persons using a decrease in the abundance or abundance ratio of bacteria belonging to the following genera as an indicator. If the abundance or abundance ratio of the following bacteria decreases more than that of healthy persons, it can be determined that the subject has developed conjunctival MALT lymphoma, or has a risk of developing conjunctival MALT lymphoma in the future.

*Bacteroides* genus bacteria (Bacteroidetes phylum, Bacteroidia class, Bacteroidales order, Bacteroidaceae family, *Bacteroides* genus)

*Clostridium* genus bacteria (Firmicutes phylum, Clostridia class, Clostridiales order, Clostridiaceae family, *Clostridium* genus)

*Deinococcus* genus bacteria (*Deinococcus-Thermus* phylum, Deinococci class, Deinococcales order, Deinococcaceae family, *Deinococcus* genus)

*Williamsia* genus bacteria (Actinobacteria phylum, Actinobacteria class, Corynebacteriales order, Williamsisaceae family, *Williamsia* genus)

*Parabacteroides* genus bacteria (Bacteroidetes phylum, Bacteroidia class, Bacteroidales order, Tannerellaceae family, *Parabacteroides* genus)

*Chryseobacterium* genus bacteria (Bacteroidetes phylum, Flavobacteriia class, Flavobacteriales order, Flavobacteriaceae family, *Chryseobacterium* genus)

*Herbaspirillum* genus bacteria (Proteobacteria phylum, Betaproteobacteria class, Burkholderiales order, Oxalobacteraceae family, *Herbaspirillum* genus)

Particularly preferably, conjunctival MALT lymphoma can be determined based on a decrease in the abundance or abundance ratio of *Bacteroides* genus bacteria or *Clostridium* genus bacteria as an indicator. Here, *Bacteroides* genus bacteria are known to produce bacterial polysaccharides and supervise maturation of immune system cells and the body during development. In the small intestine, *Bacteroides* interacts with dendritic cells in Peyer's patches of the intestine and induces a production and maturation of immunoglobulin A as a defense mechanism known as gut-associated lymphoid tissue (GALT). Therefore, presence of *Bacteroides* genus bacteria from birth is essential for maintaining intestinal immune system homeostasis and may also be useful as a local defense mechanism of ocular surface tissues. In addition, it has been reported that mucosa-associated *Clostridium* genus bacterial community plays an important role in inducing Tregs and IgA, and in suppressing inflammatory and allergic reactions. In view of the above, it can be understood that it is suggested that beneficial microbial group such as *Bacteroides* genus bacteria and *Clostridium* genus bacteria controls suppression of inflammatory response and allergic reaction as protective factors.

Further, a determination of MALT lymphoma based on changes in the microbial community structure of ocular surface tissues, particularly meibomian gland, can be performed on healthy persons using an increase in the abundance or abundance ratio of bacteria belonging to the following genera as an indicator. If the abundance or abundance ratio of the following bacteria increases more than that in healthy persons, it can be determined that the subject has developed conjunctival MALT lymphoma, or has a risk of developing conjunctival MALT lymphoma in the future.

*Delftia* genus bacteria (Proteobacteria phylum, Betaproteobacteria class, Burkholderiales order, Comamonadaceae family, *Delftia* genus)

*Clostridium* genus bacteria (Firmicutes phylum, Clostridia class, Clostridiales order, Clostridiaceae family, *Clostridium* genus)

*Brevundimonas* genus bacteria (Proteobacteria phylum, Alphaproteobacteria class, Caulobacterales order, Caulobacteraceae family, *Brevundimonas* genus)

In addition, a determination of MALT lymphoma based on changes in the microbial community structure of the ocular surface tissues, particularly the meibomian gland, can be performed in healthy persons using a decrease in the abundance or abundance ratio of bacteria belonging to the following genera as an indicator. If the abundance or abundance ratio of the following bacteria decreases more than that of healthy persons, it can be determined that the subject has developed conjunctival MALT lymphoma, or has a risk of developing conjunctival MALT lymphoma in the future.

*Lactobacillus* genus bacteria (Firmicutes phylum, Bacilli class, Lactobacillies order, *Lactobacillus* family, *Lactobacillus* genus)

*Schlegelella* genus bacteria (Proteobacteria phylum, Betaproteobacteria class, Burkholderiales order, Comamonadaceae family, *Schlegelella* genus)

Furthermore, a determination of MALT lymphoma based on changes in the microbial community structure of the ocular surface tissues, particularly the periocular skin, can be performed in healthy persons using an increase in the abundance or abundance ratio of bacteria belonging to the following genus as an indicator. If the abundance or abundance ratio of the following bacteria increases more than that in healthy subjects, it can be determined that the subject has developed conjunctival MALT lymphoma, or has a risk of developing conjunctival MALT lymphoma in the future.

*Delftia* genus bacteria (Proteobacteria phylum, Betaproteobacteria class, Burkholderiales order, Comamonadaceae family, *Delftia* genus)

In addition, a determination of MALT lymphoma based on changes in the microbial community structure of the ocular surface tissues, particularly the periocular skin, can be performed in healthy persons using a decrease in the abundance or abundance ratio of bacteria belonging to the following genus as an indicator. If the abundance or abundance ratio of the following bacteria decreases more than that in healthy subjects, it can be determined that the subject has developed conjunctival MALT lymphoma, or has a risk of developing conjunctival MALT lymphoma in the future.

*Exiguobacterium* genus bacteria (Firmicutes phylum, Bacilli class, Bacillales order, Bacillaceae family, *Exiguobacterium* genus)

In the microbiota constituting the microbiota derived from the ocular surface tissue, a similarity distance among specific groups can be used as an indicator, when it is determined the similarity distance between the microbiota of the subject and that of a healthy person is equal to or more than a certain distance, it can be determined that the subject has developed a conjunctival disease, or has a risk of developing a conjunctival disease in the future. For example, UniFrac distance analysis or the like can be used. The method of such analysis is to perform a phylogenetic tree analysis using the OTU representative sequence of the microbiota derived from the ocular surface tissue of the subject to be compared and that of a healthy person, and to calculate a difference in the microbial community structures as a distance (UniFrac distance) from the length of branches of OTU shared between both microbiotas and from the ratio of branches specific to each microbiota, and a similarity between the microbiotas can be presented 0 (100% similar) to 1 (100% dissimilar) of distance (UniFrac distance). Further, a two-dimensional scatter diagram may be created by principal coordinate analysis based on UniFrac distance. A determination whether the similarity distance between the microbiota of the subject and that of healthy persons is equal to or greater than a certain distance can be determined by, for example, comparison with reference data, based on which the group of developing conjunctival disease or the group of healthy persons is close to the similarity distance of the subject. When the distance of the group of developing conjunctival disease is close to that of the subject, it can be determined that the subject has developed a conjunctival disease or has a risk of developing the disease in the future. In addition, the above two-dimensional scatter diagram may be used, and when the microbiota of the subject on the two-dimensional scatter diagram is located relatively closer to the group of developing a conjunctival disease compared to the group of healthy persons, it can be determined that the subject has developed a conjunctival disease or has a risk of developing a conjunctival disease in the future.

In the method of detecting a conjunctival disease according to the present embodiment, a microbial species that can be an indicator of a change in the microbial community structure of the ocular surface tissue can be used as a disease biomarker for detecting a conjunctival disease, and such a disease biomarker also serves as a part of the present invention. It can be also used as a conjunctival disease detection kit for detecting a conjunctival disease by detecting a change in the microbial community structure, and such a disease detection kit also serves as a part of the present invention. For example, it can be configured to include an oligonucleotide probe and a primer for a microbe-specific gene, or a specific antibody, and the like.

(Aging Biomarker)

The aging biomarker according to the present embodiment provides information on an aging state of a living organism by a change in a balance of the microbiota existing in the ocular surface tissue. That is, the aging biomarker according to the present embodiment is based on the finding that a change in the microbial community structure of the microbiota existing in the ocular surface tissue correlates with aging.

The aging biomarker according to the present embodiment means a factor that fluctuates depending on aging, that is, lapse of survival time, and can predict an aging state such as the degree of aging. Aging is a change in biological performance that occurs after a stage of maturity, means a decrease in functions that appear at all levels of individuals, organs, tissues, and cells, and includes not only aging based on calendar age but also aging based on biological age. Also, it does not matter whether aging is physiological aging or pathological aging. Therefore, the aging biomarker according to the present embodiment serves as an indicator of not only a physiological aging state but also a pathological aging state. Here, physiological aging means a physiological function decline inevitably progressing with aging, and pathological aging means a function decline that causes a pathological condition due to abnormally accelerated aging or the like.

Since the aging biomarker according to the present embodiment serves as an indicator of a pathological aging state, it can be used as an indicator of the onset and progression of a disease in which an abnormality occurs in a body as a result of aging-related changes. Such diseases include diseases in which incidence increases with age, and include conjunctival MALT lymphoma, pterygium, dry eye, conjunctival relaxation, glaucoma, age-related macular degeneration (AMD), and the like.

The aging biomarker according to the present embodiment uses a change in the microbial community structure of the microbiota in the ocular surface tissue specimen derived from the subject, as an indicator. The details of the ocular surface tissue specimen and of the method of sampling it are as described in the above section (Method of Detecting Conjunctival Disease).

The detection of the change in the microbiota in the ocular surface tissue specimen using the biomarker according to the present embodiment can be performed using a known technique in the art, and the details thereof are as described in the above section (Method of Detecting Conjunctival Disease).

The aging biomarker according to the present embodiment uses a change in the microbial community structure of the microbiota derived from the ocular surface tissue of the subject, as an indicator. For example, in bacteria constituting the microbiota derived from the ocular surface tissue, bacteria belonging to a specific phylum, class, order, family, genus, or species whose abundance or abundance ratio varies depending on aging can be used as the aging biomarker. Here, the abundance ratio can be a ratio, a difference, a sum, or a product of the abundance ratios of a plurality of bacteria belonging to a specific phylum, class, order, family, genus, or species. The aging biomarker can be bacteria at any level of the phylum, class, order, family, genus, and species. Also, it may be bacteria at the level of 1 phylum, class, order, family, genus, or species, or bacteria at the level of a plurality of phyla, classes, orders, families, genera, or species.

For example, bacteria belonging to the following families can be used as the aging biomarker, all of which are indigenous bacteria of ocular surface tissues.

Corynebacteriaceae family bacteria (Actinobacteria phylum, Actinobacteria class, Corynebacteriales order, Corynebacteriaceae family)

Propionibacteriales family bacteria (Actinobacteria phylum, Actinobacteria class, Propionibacteriales order, Propionibacteriales family)

The abundance, abundance ratio and the like of Corynebacteriaceae family bacteria and Propionibacteriales family bacteria are correlated with the aging state of the living organism. Specifically, with regard to Corynebacteriaceae family bacteria, the abundance, abundance ratio and the like increase with aging, while, with regard to Propionibacteriales bacteria, the abundance, abundance ratio and the like decrease with aging. Therefore, Propionibacteriales family bacteria predominate in the young people, while Corynebacteriaceae family bacteria predominate in old people. Therefore, when the abundance, the abundance ratio and the like of Propionibacteriales family bacteria in the ocular surface tissue specimen of the subject are predominant, it can be determined that the subject is in an aging state, and conversely, when the abundance, the abundance ratio and the like of Corynebacteriaceae family bacteria are predominant, it can be determined that the subject is not in an aging state.

Specifically, a ratio of the abundance ratios of a plurality of bacteria whose abundance fluctuates in an aging-dependent manner can be used as an aging biomarker. For example, the ratio of Propionibacteriaceae family bacteria/Corynebacteriaceae family bacteria is used as the aging biomarker. If such a ratio is high, it can be determined that the subject is in an aging state. For example, in the ratio of Propionibacteriaceae family bacteria/Corynebacteriaceae family bacteria, it can be configured to set a cut-off value and to determine the aging state of the subject. Young people have higher abundance and abundance ratio of Propionibacteriaceae family bacteria, and the abundance and abundance ratio of Corynebacteriaceae family bacteria increase with aging. Therefore, if it is smaller than the set cut-off value, it can be determined that the subject is in an aging state. The cutoff value can be set appropriately according to the purpose of detection and the like, and can be set to, for example, 1. Further, specifically, a difference in the abundance ratios of a plurality of bacteria whose abundance fluctuates in an aging-dependent manner can be used as the aging biomarker. For example, the difference of Propionibacteriaceae family bacteria-Corynebacteriaceae family bacteria can be used as the aging biomarker, and if such a difference is small, it can be determined that the subject is in an aging state. Therefore, in the difference of Propionibacteriaceae family bacteria-Corynebacteriaceae family bacteria, it can be configured to set a cut-off value and determine the aging state of the subject, and if it is smaller than the set cut-off value, it can be determined that the subject is in the aging state. The cutoff value can be set appropriately according to the purpose of detection and the like, and can be set to, for example, 0. Furthermore, the degree of aging (e.g. +5 years older relative to actual age, and the like) can be determined based on the ratio of Propionibacteriaceae family bacteria/Corynebacteriaceae family bacteria and/or the difference of Propionibacteriaceae family bacteria-Corynebacteriaceae family bacteria. That is, with regard to being in the aging state, in addition to the qualitative evaluation of being in the aging state having a high risk of a conjunctival disease, a method of quantitatively evaluating the aging degree with respect to the actual age is also included.

In the microbiota constituting the microbiota derived from the ocular surface tissue, a similarity distance among specific groups can be used as an indicator. When the similarity distance between the microbiota of the subject and, for example, that of a young healthy person is equal to or greater than a certain distance, it can be determined that the subject is in the aging state or the like. For example, UniFrac distance analysis or the like can be used, the details are as described in the above section (Method of Detecting Conjunctival Disease).

The aging biomarker according to the present embodiment can be used to detect the aging state (risk of a conjunctival disease) of the subject, and such an aging state detection method also forms a part of the present invention. For example, it is a method of detecting a conjunctival disease, the method comprising a step of comparing a microbial community structure of a microbiota included in an ocular surface tissue specimen sampled from a healthy young person with a microbial community structure of a microbiota included in an ocular surface tissue specimen sampled from the subject to detect an ocular surface tissue specimen to be evaluated as being a conjunctival disease based on a change in the microbial community structure between the healthy young person and the subject. The biomarker according to the present embodiment can be used as an indicator on the change in the microbial community structure. The details of the step can be performed according to the above section (Method of Detecting Conjunctival Disease).

EXAMPLES

[Example 1] Change in Microbiota in Conjunctival MALT Lymphoma (Bacterial Biota)

In this example, a relationship between a change in the microbiota of the ocular surface tissue and the onset of conjunctival MALT lymphoma was examined. Specifically, the microbial community structure (bacteria) contained in a specimen sampled from human ocular surface tissues was analyzed by 16S rRNA gene, and healthy persons were compared with persons suffering from conjunctival MALT lymphoma.

[Disease Group and Healthy Group]

Between 2015 and 2017, 25 persons (50 eyes) diagnosed as having conjunctival MALT lymphoma by biopsy at Osaka University Hospital were included in a disease group (Table 1). From the disease group, persons with obvious ocular surface diseases, persons who have recently worn contact lenses, persons who have taken systemic or topical antibiotics or eye prescription drugs in the past 12 months, persons who had a history of eye surgery in the past 12 months, persons with ocular infection, persons with dry eye symptoms, persons with systemic diseases such as diabetes, and persons who smoked were excluded. The disease group consisted of 7 men and 18 women with an average age of 61.7±15.6 years. As a control, 25 healthy volunteers (50 eyes) were similarly examined as a healthy group. The healthy group consisted of 7 men and 18 women with an average age of 58.3±13.0 years. Table 1 shows clinical data and backgrounds of the disease group. Out of 25 persons in the disease group, 5 persons had a history of chemotherapy and radiotherapy, 6 persons had only a history of chemotherapy, and 3 persons had only a history of radiotherapy. Five persons had gastric lesions (2 cases with gastric MALT lymphoma, 1 case with gastric polyp, 1 case with gastric ulcer, 1 case with gastric cancer). The mean observation period was 50.0±6.2 months (5 to 93 months).

TABLE 1

| Identification Number | Age | Gender | Eyes | Chemotherapy | Radiotherapy | Gastric lesions | Progress period (Months) |
|---|---|---|---|---|---|---|---|
| 1 | 42 | Female | Right | No | No | No | 48 |
| 2 | 78 | Female | Both | No | No | No | 22 |
| 3 | 26 | Female | Both | No | No | No | 18 |
| 4 | 91 | Female | Both | Yes | Yes | No | 93 |
| 5 | 45 | Female | Both | Yes | No | No | 20 |
| 6 | 79 | Female | Both | No | No | MALT lymphoma | 7 |
| 7 | 73 | Female | Left | Yes | Yes | No | 23 |
| 8 | 85 | Female | Right | Yes | No | No | 63 |
| 9 | 58 | Female | Left | No | No | No | 74 |
| 10 | 78 | Male | Left | Yes | No | Gastric cancer | 86 |
| 11 | 51 | Male | Right | No | Yes | Gastric ulcer | 57 |
| 12 | 72 | Male | Left | No | Yes | No | 53 |
| 13 | 74 | Female | Both | Yes | Yes | No | 89 |
| 14 | 78 | Male | Both | Yes | No | Gastric polyp | 64 |
| 15 | 52 | Female | Right | No | No | No | 66 |
| 16 | 50 | Female | Right | No | No | No | 15 |
| 17 | 63 | Male | Right | Yes | Yes | No | 90 |
| 18 | 61 | Female | Both | No | Yes | No | 85 |
| 19 | 57 | Male | Both | Yes | Yes | MALT lymphoma | 93 |
| 20 | 47 | Female | Left | Yes | No | No | 48 |
| 21 | 42 | Female | Left | No | No | No | 7 |
| 22 | 65 | Male | Right | Yes | No | No | 55 |
| 23 | 67 | Female | Right | No | No | No | 65 |
| 24 | 51 | Female | Left | No | No | No | 5 |
| 25 | 58 | Female | Right | No | No | No | 5 |

[Method]

(Sample Collection and DNA Isolation)

Specimens were sampled in a clean room for ophthalmic treatment. Specimens were sampled from the superior and inferior conjunctival fornix of both eyes with DNA swab (Osaki Sterilized Cotton Swabs S0475-10, JAPAN) after each person of the above disease group and healthy group was instilled with sterilized local anesthetic proparacaine at baseline (reference time) and 1 month later. Specimens were similarly sampled from the hand, meibomian gland, and periocular skin to compare the conjunctiva with other sites. Therefore, the following experiments were performed on the specimens sampled from 4 places: conjunctiva, hand, meibomian gland, and periocular skin. Each sampled specimen was transferred to a tube (Eppendorf, Fremont, CA) and was frozen at −80 degrees Celsius until DNA extraction. DNA extraction was performed using PowerSoil (registered trademark) DNA Isolation Kit (MoBio, Carlsbad, CA) according to the manufacturer's instructions. Each extracted genomic DNA was eluted in 100 μl of a kit elution buffer and was stored at −20 degrees Celsius until analysis.

(Sequencing and Sequence Data Processing of 16S rRNA Gene)

Each amplicon was prepared using a primer set targeting V1-V2 region of the 16S rRNA gene (27Fmod: 5'-AGRGTTTGATCMTGGCTCAG-3' (R=G or A, M=A or C) (SEQ ID NO: 1), and 338R: 5'-TGCTGCCTCCCGTAG-GAGT-3' (SEQ ID NO: 2) according to the "Illumina 16S Metagenomic Sequencing Library Preparation Guide". Pair-end sequencing of the prepared amplicon was performed with MiSeq (Illumina) using MiSeq v2 500 cycle kit. Paired end sequences were merged using PEAR (sco.h-its.org). Subsequently, quality trimming was performed for the merged read using BBtrim (bbmap.sourceforge.net). Twenty thousand reads per sample were randomly selected using random_sequence_sample.pl (ualberta.ca) for further analysis. The processed reads were clustered into OTUs with a sequence similarity threshold defined at 97% using UCLUST version 1.2.22q. The representative sequence of each OTU was then taxonomically classified by using RDP Classifier version 2.2 with Greengenes 13_8 database. Bioinformatics pipeline QIIME version 1.9.1 was used as the informatics environment for all relevant processing of raw sequencing data.

(Statistical Analysis)

Data are shown as mean+SE. Statistical analysis was performed using JMP software version 9.0 (SAS Inc, Cary, North Carolina, USA) and the R software environment (public domain, cran.r-project.org) version 3.1.3. The classified data were analyzed by linear discriminant analysis (LDA) effect size (LefSe) (Harvard group) analysis to find out distinctive characteristics of the microbiota between the disease group and the healthy group. ($\alpha<0.01$).

[Result]

(Result of Sequencing and Data Processing of 16S rRNA Gene and Stability of Bacterial Composition)

A total of 18,851,375 raw 16S rRNA gene sequences were obtained, which yielded a total of 13,094,927 pairs of paired end sequences after quality filtering, with an average of 53,231 sequences per specimen. To verify stability of the microbiota at the 4 sites from which specimens were sampled, the bacterial composition of the specimens sampled at baseline and those sampled 1 month after the baseline were compared for the healthy group. The results are shown in FIG. 1. FIG. 1 shows the relative abundance of each bacterial species at each site. As a result, no significant change was observed in the bacterial composition at the baseline and one month after the baseline at any of the sites verified this time. From the results, it could be understood that stable microbiota was formed at the 4 sites examined this time, and it was found that stable microbiota such as intestinal microbiota also existed in ocular surface tissues such as conjunctiva.

Next, effects of gender and left-right bias on the bacterial composition of the microbiota existing in the conjunctiva were examined. The results are shown in FIGS. 2A and 2B. FIGS. 2A and 2B show the main bacteria constituting the microbiota of the healthy group and that of the disease group, and the relative abundance ratios thereof are shown in the graphs. As a result, no significant change was observed in the gender and left/right bias in both the healthy group (FIG. 2A) and the disease group (FIG. 2B).

(Diverse and Similarity of Microbiota)

Figure 3:
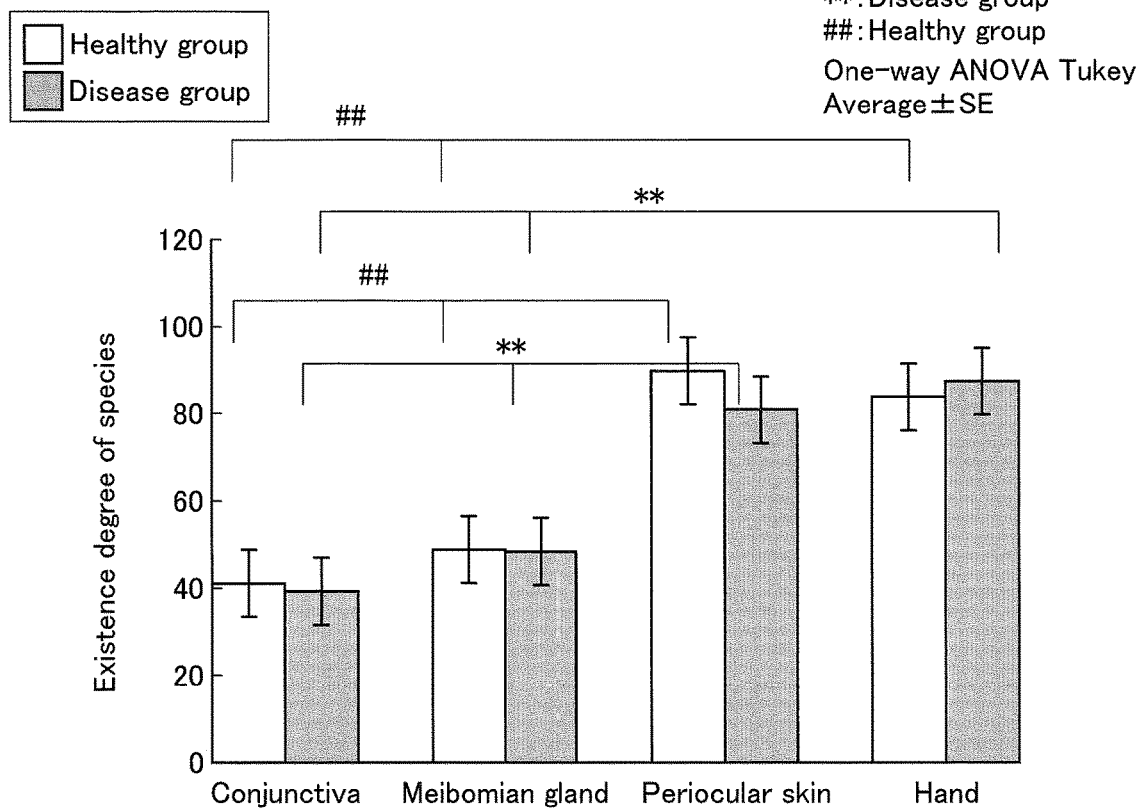
FIG. 3 is a graph showing a result of verifying α diversity of microbiotas among 4 sites (conjunctiva, meibomian gland, periocular skin, and hand) from which specimens were sampled.

Microbiota diversity at the 4 sites was examined at family level in the healthy group and the disease group. The result is shown in FIG. 3. From the result, the numbers of conjunctiva, meibomian gland, periocular skin and hand microbiotas in the healthy group were 41.2±0.86 (range 33 to 52), 48.6±2.31 (range 32 to 65), 89.4±5.14 (range 50 to 131), and 83.5±5.11 (range 38 to 137), respectively. The numbers of conjunctiva, meibomian gland, periocular skin and hand microbiotas in the disease group were 39.4±0.86 (range 30 to 51), 48.2±2.48 (range 31 to 79), 80.8±6.09 (range 47 to 187), 87.4±6.57 (range 55 to 140), respectively. Statistical analysis between the healthy group and the disease group was performed by one-way ANOVA using Tukey post hoc analysis. There was no significant difference in a-diversity of the microbiota between the conjunctiva of the healthy group and that of the disease group. The conjunctiva and meibomian gland showed lower a-diversity than the periocular skin and hand (P<0.01), while no significant difference was observed between conjunctiva and meibomian gland. From the result, it can be understood that the microbiota of the conjunctiva and the meibomian gland has less diversity than that of the body surface.

Figure 4A:
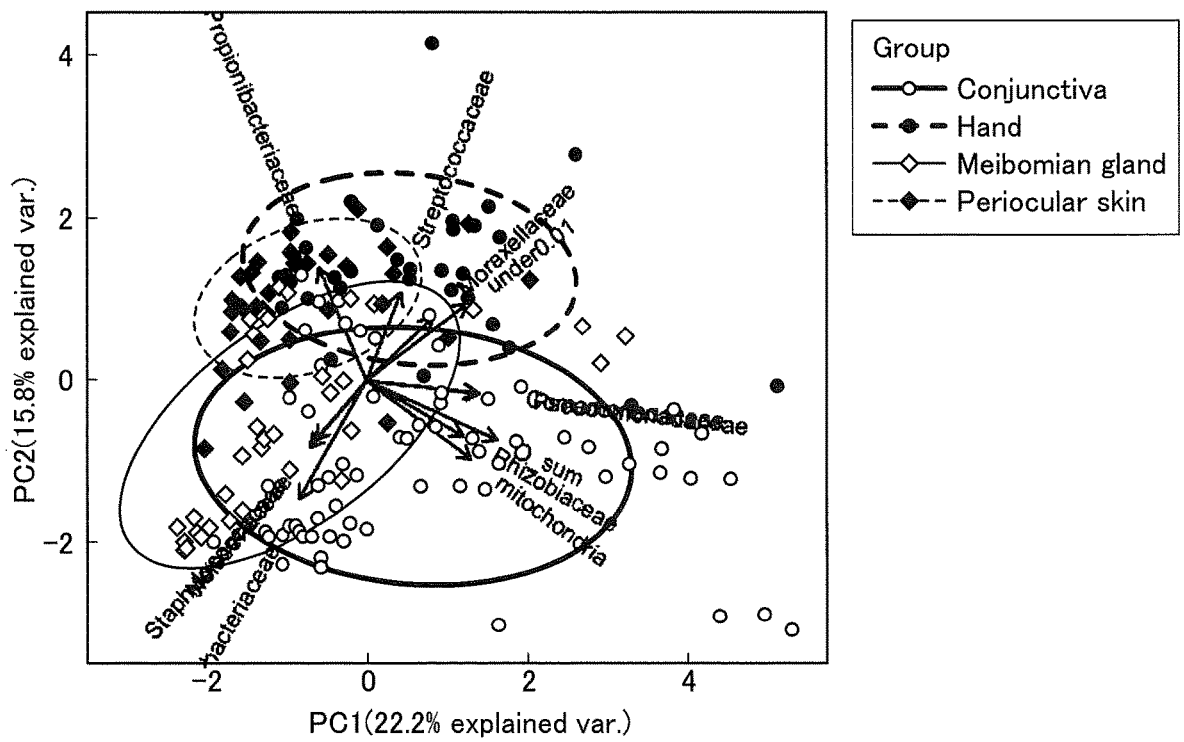
FIG. 4A is a graph showing results of verifying β diversity of microbiotas by PCA among 4 sites (conjunctiva, meibomian gland, periocular skin, and hand) from which specimens were sampled, and showing results of the healthy group.
Figure 4B:
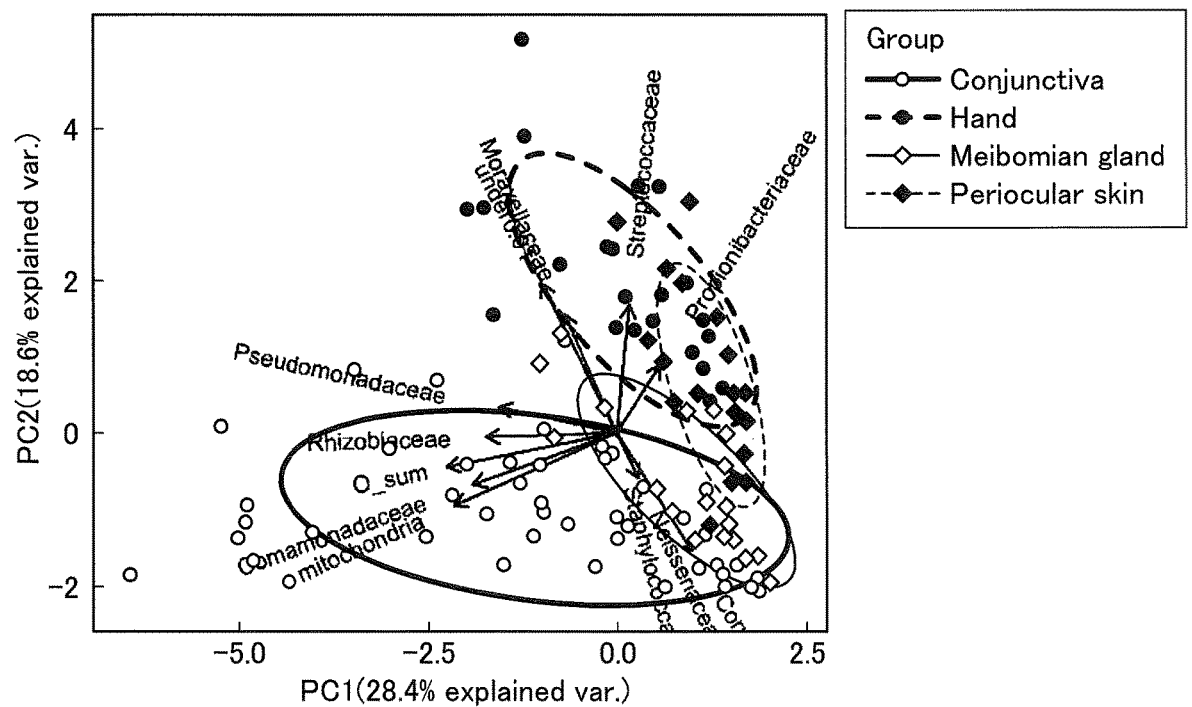
FIG. 4B is a graph showing results of verifying α diversity of microbiotas by PCA among 4 sites (conjunctiva, meibomian gland, periocular skin, and hand) from which specimens were sampled, and showing results of the disease group.

Subsequently, in order to examine a similarity of the bacterial groups that constitute the microbiota in terms of β diversity, principal component analysis (PCA) was performed, and clustering was performed at the 4 sites from which specimens were sampled for top 11 kinds of bacteria in composition. The results are shown in FIGS. 4A and 4B. From the results, distances of the conjunctiva, the meibomian gland, the periocular skin, and the hand from which specimens were sampled in the healthy group and the disease group were clarified at a family level. Specifically, in the healthy group and the disease group, relatively small distances were observed between the conjunctiva and the meibomian gland, and between the periocular skin and the hand. There was a large distance between the conjunctiva and the hand. On the other hand, a separation between the conjunctiva and the hand was understood on the PCA plot.

(Difference in the Partial Microbiota at a Genus Level in the Healthy Group and the Disease Group at 4 Parts of the Body Analyzed by LEfSe)

LEfSe analysis was performed to verify a difference in bacterial composition in the microbiota between the healthy group and the disease group. The results are shown in FIG. 5 as bar graphs showing LDA scores and phylogenetic diagrams including hierarchy of biological classification. In the bar graphs, the bacteria that significantly increase and decrease in the disease group were classified at a genus level, and the LDA scores were plotted on the phylogenetic diagrams. As a result, in the conjunctiva of the disease group compared to the healthy group, presences of *Delftia* genus bacteria, *Xylophilus* genus bacteria, *Simplicispira* genus bacteria, *Rothia* genus bacteria, and *Xanthomonas* genus bacteria are significantly higher, and presences of *Bacteroides* genus bacteria, *Clostridium* genus bacteria, *Deinococcus* genus bacteria, *Williamsia* genus bacteria, *Parabacteroides* genus bacteria, *Chryseobacterium* genus bacteria, and *Herbaspirillum* genus bacteria were significantly lower. On the other hand, in the meibomian gland, presences of *Delftia* genus bacteria, *Clostridium* genus bacteria, and *Brevundimonas* genus bacteria were significantly higher, and presences of *Schnedlella* genus bacteria and *Lactobacillus* genus bacteria were significantly lower. In the periocular skin, a presence of *Delftia* genus bacteria was significantly higher and a presence of *Exiguobacterium* genus bacteria was significantly lower.

Figure 6A:
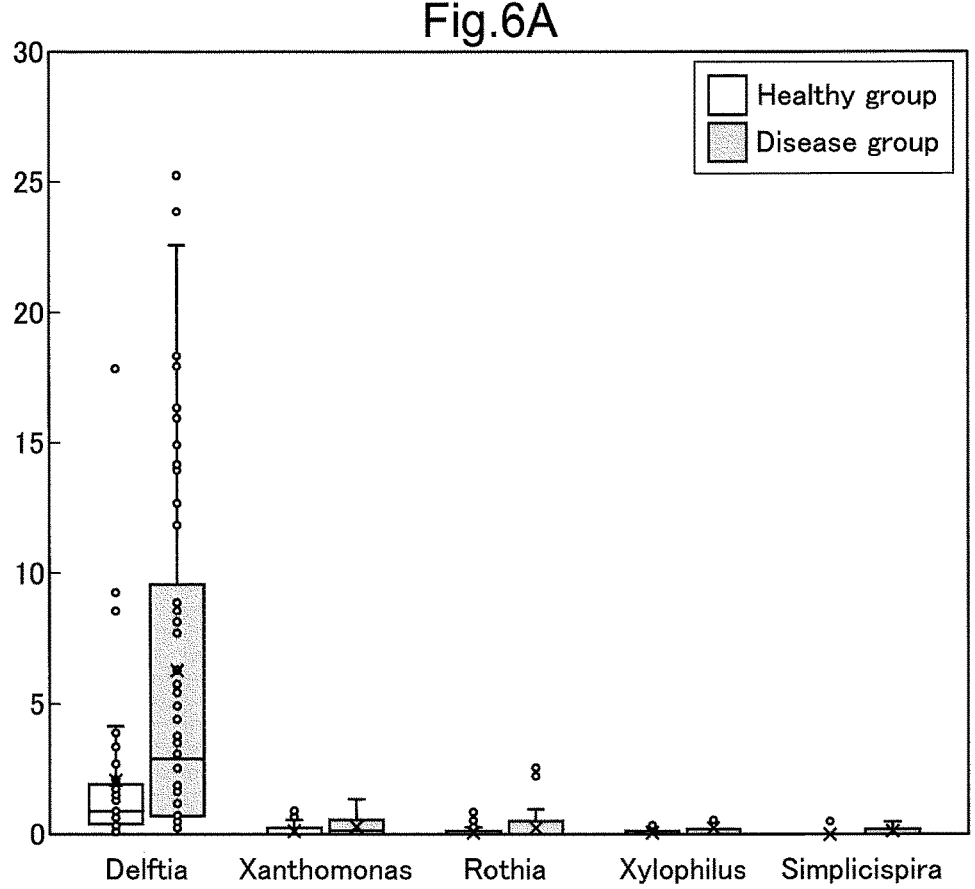
FIG. 6A is a box-and-whisker plot showing results of more detailed examination of differences in bacterial compositions of microbiotas from the healthy group and that from the disease group and showing abundance ratio for each bacterial species, and is showing results of statistically higher abundance ratios of bacterial species in the disease group than that in the healthy group.
Figure 6B:
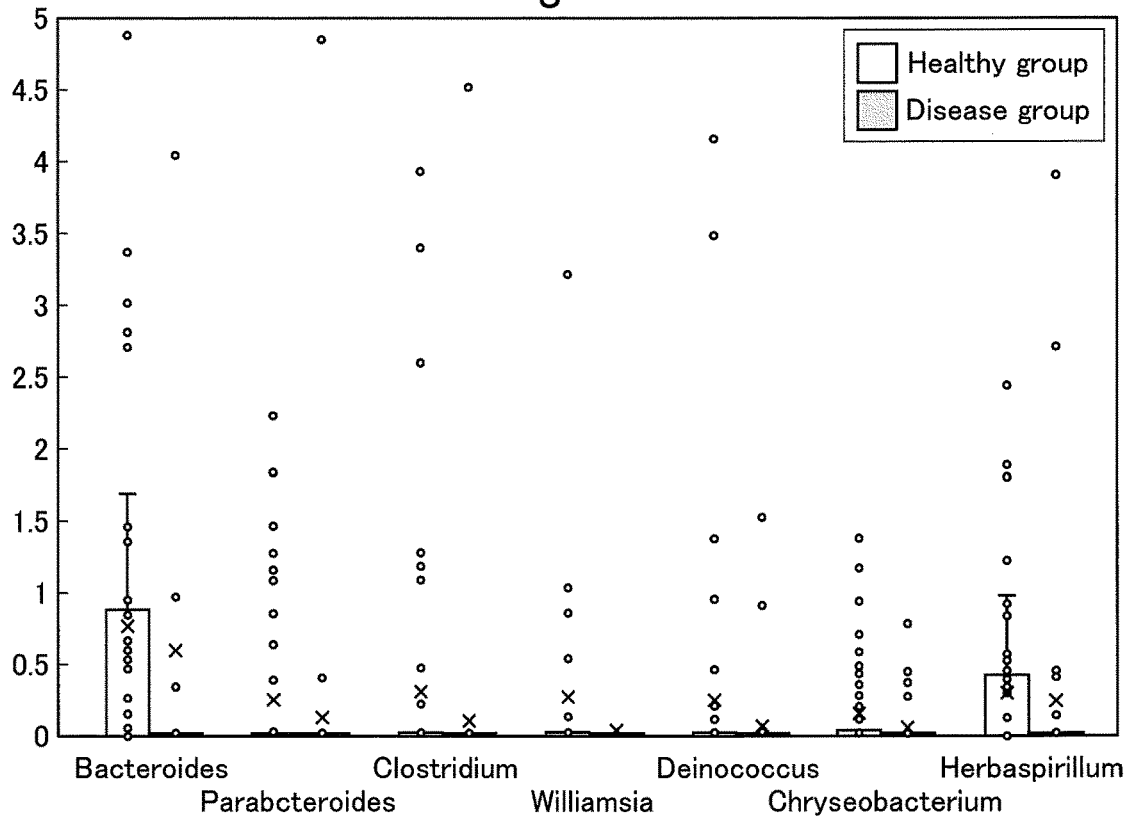
FIG. 6B is a box-and-whisker plot showing results of more detailed examination of differences in bacterial compositions of microbiotas from the healthy group and that from the disease group and showing abundance ratio for each bacterial species, and is showing results of statistically lower abundance ratios of bacterial species in the disease group than that in the healthy group.

Further, a difference in bacterial composition in the microbiota between the healthy group and the disease group was examined in more detail. The results are shown in FIGS. 6A and 6B, and the abundance ratio for each bacterial species is shown by a box-and-whisker plot. Here, in FIG. 6A and FIG. 6B, a relative occupancy ratio (%) of each bacterium with respect to the bacterium group existing at each site is shown on the vertical axis. As a result, a presence of *Delftia* genus bacteria was detected in many in the healthy group and the disease group, and presences of *Xylophilus* genus bacteria, *Simplicispira* genus bacteria, *Rothia* genus bacteria, and *Xanthomonas* genus bacteria were extremely rare in both groups (FIG. 6A). Then, it was confirmed that presences of the above 5 types of bacteria in the disease group were statistically higher than that in the healthy group. On the other hand, presences of *Bacteroides* genus bacteria, *Parabacteroides* genus bacteria, *Clostridium* genus bacteria, *Williamsia* genus bacteria, *Deinococcus* genus bacteria, *Chryseobacterium* genus bacteria, and *Herbaspirillum* genus bacteria were mainly detected in the healthy group and rare in the disease group (FIG. 6B). Then, it was confirmed that presences of the above 7 types of bacteria in the disease group were statistically lower than that in the healthy group.

From the above results, it could be understood that an indigenous microbiota exists in the body's internal habitat environment of each parts tested this time, and that the indigenous microbiota also exists on the ocular surface such as the conjunctiva, preventing invasion of foreign bacteria. In addition, it was confirmed that there was a difference between the microbiota of healthy persons and that of persons suffering from conjunctival MALT lymphoma in bacterial composition. Therefore, it can be understood that, by analyzing the microbial community structure of the ocular surface tissue of subjects, subjects who have developed conjunctival MALT lymphoma, or subjects who have a risk of developing conjunctival MALT lymphoma in the future can be detected based on the abundance, the abundance ratio and the like of the constituent microbes.

As confirmed above, it was shown that, in the disease group of conjunctival MALT lymphoma, specific bacterial species in the microbial community structure of the microbiota, specifically, *Delftia* genus is significantly higher, and *Bacteroides* genus and *Clostridium* genus are lower than that in the healthy group. Thus, *Delftia* genus bacteria may have a pathophysiological role in the development of conjunctival MALT lymphoma, and *Bacteroides* genus bacteria and *Clostridium* genus bacteria may be protective factors for conjunctival MALT lymphoma. Thus, it is considered that the microbiota of the conjunctiva constantly fluctuates and maintains local homeostasis, and that dysbiosis may play an important role in the pathophysiology of conjunctival MALT lymphoma.

[Example 2] Change in Tear Fluid Property in Conjunctival MALT Lymphoma

In this example, a relationship between changes in tear fluid properties and the onset of conjunctival MALT lymphoma was examined. Specifically, pH and IgA concentration of tear fluid in human eyes were analyzed, and healthy persons were compared with persons suffering from conjunctival MALT lymphoma.
[Change in Tear Fluid pH]

In Example 1, it was confirmed that, in the disease group of conjunctival MALT lymphoma, bacteria belonging to *Delftia* genus were significantly higher in the microbial community structure of the microbiota than that in the healthy group. It has been reported that *Delftia* genus bacteria are bacteria that exist in soil, water, and living environment (Mahmood S. et al., J. Clin. Microbiol., 2012, 50 (11), p3799-3800), and has an ability to modify organic acid and amino acid residues (Sabine Leibeling et al., Environ. Sci. Technol., 2010, 44 (10), p3793-3799). Based on such a characteristic of *Delftia* genus bacteria, it was hypothesized that the pH of tear fluid of persons suffering from conjunctival MALT lymphoma in which *Delftia* genus bacteria significantly increase in the microbial community structure decreases, and the following examination was performed.
[Method]

A disease group and healthy persons were selected in the same manner as in Example 1, and the pH of tear fluid of the disease group (N=28) and the healthy group (N=26) was measured using a pH meter (LAQUA twin B-731: HORIBA, Ltd.). It was analyzed by Wilcoxon rank sum test whether there was a significant difference between both the groups.
(Result)

Figure 7:
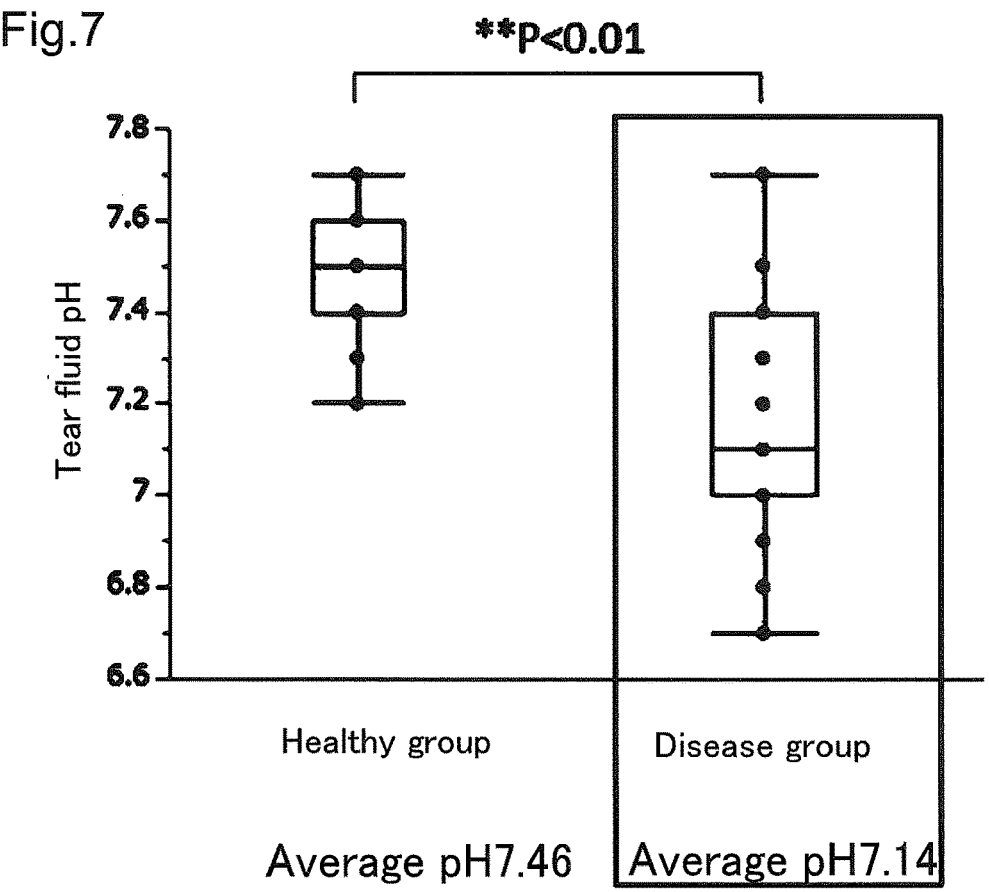
FIG. 7 is a box-and-whisker plot showing results of verifying a difference between tear fluid property derived from the healthy group and that from the disease group, and showing results of measured tear fluid pH.

The result is shown in FIG. 7. As a result, the mean pH was 7.46 in the healthy group, whereas it was 7.14 in the disease group, and it could be confirmed that the pH of tear fluid of persons suffering from conjunctival MALT lymphoma significantly decreased.
[Change in Tear Fluid IgA Concentration]

In Example 1, it was confirmed that, in the disease group of conjunctival MALT lymphoma, the bacteria belonging to *Bacteroides* genus and *Clostridium* genus were significantly lower in the microbial community structure of the microbiota than that in the healthy group. It has been reported that *Bacteroides* genus bacteria constitute a gut microbiota, activate regulatory T cells (T-reg)/Th17, and trigger control of an inflammatory response (Abby L. Geis et al., Cancer Discov., 5 (10), p1098-1109). In addition, there is also another report that it is involved in antibody production and inflammatory reaction control (Rol N. et al., J. Biol. Chem., 2012, 287 (47), p40074-40082, Sara Omenetti et al., Front. Immunol., 2015, 6, Article 639). On the other hand, with respect to *Clostridium* genus bacteria, it is reported that T-reg is induced by administration of such *Clostridium* genus bacteria, and that it is involved in maintaining immunity (Taylor Feehley et al., Curr. Opin. Lmmunol., 2014, 31, p79-86). In addition, there is also another report that it is involved in control of allergy reaction (Ouwehand A C. Et al., World J. Gastroenterol., 2009, 15 (26), 3261-3268, and Stefka A T. Et al., Proc. Natl. Acad. Sci. USA, 111 (36), p13145-13150). From such characteristics of *Bacteroides* genus bacteria and *Clostridium* genus bacteria, it was hypothesized that persons suffering from conjunctival MALT lymphoma in which *Bacteroides* genus bacteria and *Clostridium* genus bacteria significantly decrease in the microbial community structure have reduction in immune mechanism, and the following examination was performed.
(Method)

A disease group and healthy persons were selected in the same manner as in Example 1, and the IgA concentration contained in tear fluid of the disease group (N=28) and the healthy group (N=26) was measured by ELISA kit for human IgA measurement. Then, it was analyzed by Wilcoxon rank sum test whether there was a significant difference between both the groups.
(Result)

Figure 8:
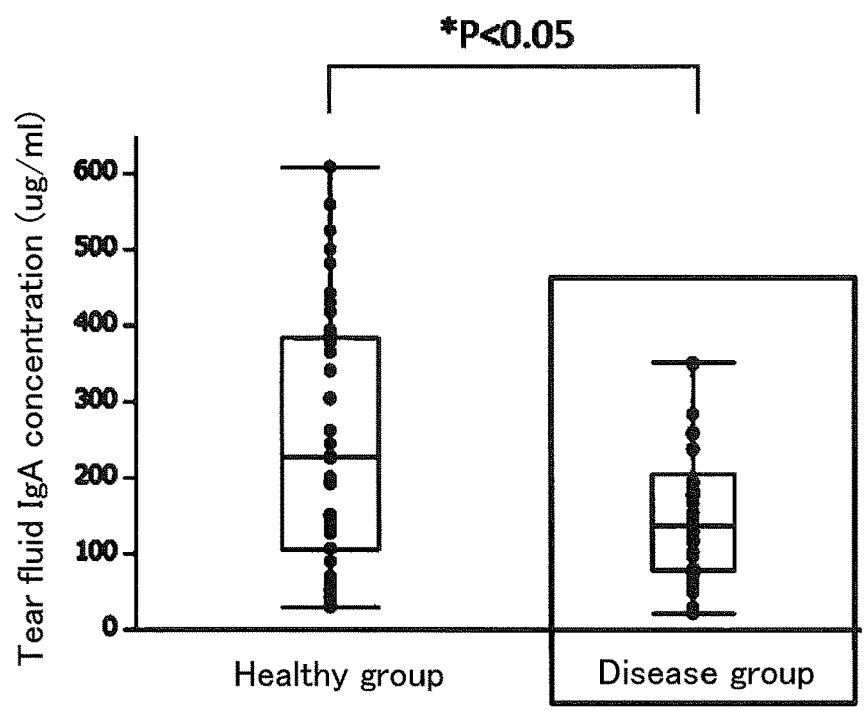
FIG. 8 is a box-and-whisker plot showing results of verifying a difference between tear fluid property derived from the healthy group and that from the disease group, and showing results of measured tear fluid IgA concentration.

The result is shown in FIG. 8. As a result, tear fluid IgA concentration in the disease group was significantly lower than that in the healthy group. With this, it can be confirmed that the concentration of IgA contained in tear fluid of persons suffering from conjunctival MALT lymphoma significantly decreased, and it can be understood that the immune function is reduced.

Changes in the microbial community structure of the microbiota in ocular surface tissues may lead to changes in a conjunctival environment. In the conjunctival MALT lymphoma examined this time, *Delftia* genus bacteria are an aggressive factor that can be a source of inflammation as a pathogen, and *Bacteroides* genus bacteria and *Clostridium* genus bacteria may be a protective factor through control of activation and inflammatory response of T-reg/Th17, induction of production of IgA, or the like. In the microbial community structure, a balance change in *Delftia* genus bacteria as an aggressive factor, and *Bacteroides* genus bacteria and *Clostridium* genus bacteria as protective factors may be involved in the onset of conjunctival MALT lymphoma.

Based on the above results, multivariate analysis of 3 kinds of bacteria (*Delftia* genus bacteria, *Bacteroides* genus bacteria, and *Clostridium* genus bacteria) which are involved in the onset of conjunctival MALT lymphoma, was performed. Here, analysis was performed on age, gender, and lateral clinical parameters of persons suffering from conjunctival MALT lymphoma, and a p-value was calculated. If the p-value was 0.05 or less, it was determined that there was a correlative relationship. The results are shown in Table 2. As shown in Table 2, no significant difference was observed in the clinical parameters examined this time, and it is supported that the change in the microbial community structure confirmed in Example 1 does not depend on age, gender, or laterality, and is specific to conjunctival MALT lymphoma. Therefore, it is supported that changes in the community structure of microbes including *Delftia* genus bacteria, *Bacteroides* genus bacteria, and *Clostridium* genus bacteria are involved in the onset of conjunctival MALT lymphoma.

TABLE 2

| Clinical parameters | Microbes | P-value |
| --- | --- | --- |
| Age (60 years or less vs more than 60 years) | *Delftia* genus | 0.6052 |
| | *Bacteroides* genus | 0.8175 |
| | *Clostridium* genus | 0.6022 |
| Gender (male vs female) | *Delftia* genus | 0.9565 |
| | *Bacteroides* genus | 0.0842 |
| | *Clostridium* genus | 0.9744 |
| Laterality (both eyes vs one eye) | *Delftia* genus | 0.1138 |
| | *Bacteroides* genus | 0.3618 |
| | *Clostridium* genus | 0.3944 |

[Example 3] Change in Microbiota in Conjunctival MALT Lymphoma (Fungal Biota)

In this example, a relationship between a change in the microbiota of ocular surface tissues and the development of conjunctival MALT lymphoma was examined. Specifically, microbial community structures (fungi) contained in specimens sampled from human ocular surface tissues were analyzed by ITS region genes, and healthy persons were compared with persons suffering from conjunctival MALT lymphoma.
(Method)

A disease group and healthy persons were selected in the same manner as in Example 1. For the disease group (N=50) and the healthy group (N=50), the microbiota of the ocular surface tissue (conjunctiva) was analyzed by (sample collection and DNA isolation), (ITS regional sequencing and data processing) and (statistical analysis) in the same manner as in Example 1. For the ITS region sequencing, each amplicon was prepared by using primer sets targeting the ITS region in rRNA (ITS1-F: 5'-CTTGGTCATTTAGAG-GAAGTAA-3' (SEQ ID NO: 3)) and (ITS2: 5'-GCATCGAT-GAAGAACGCAGC-3' (SEQ ID NO: 4)), and sequencing was performed with MiSeq (Illumina) using MiSeq v2 500 cycle kit.

(Result)

Figure 9:
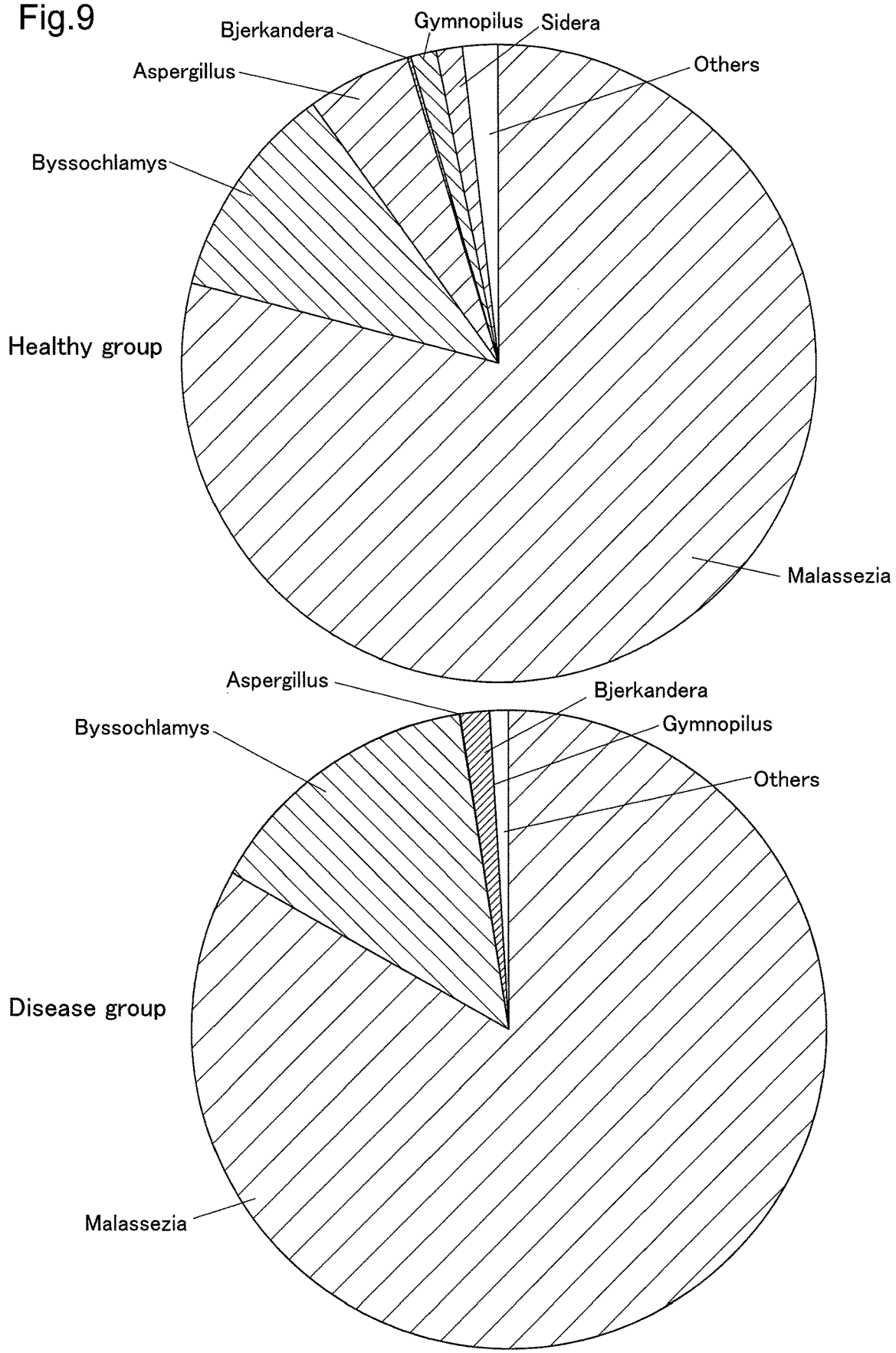
FIG. 9 shows results of a comparison of fungal compositions of microbiotas of specimens sampled from conjunctivae between the healthy group and the disease group, and shows abundance ratio of each fungal species.
Figure 10A:
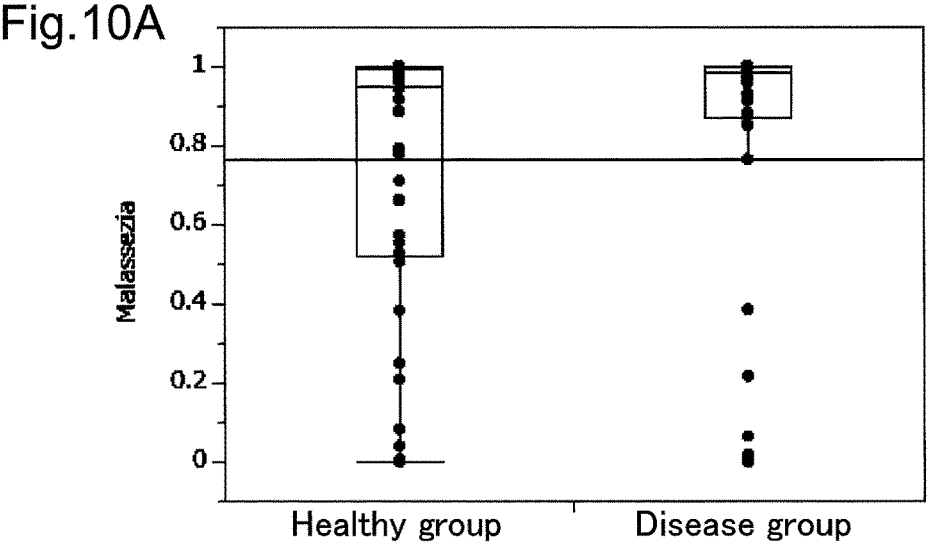
FIG. 10A is a box-and-whisker plot showing a result of further detailed examination of a difference between the bacterial composition of the microbiota of the conjunctiva from the healthy group and that from the disease group, and is showing a result in which abundance ratios of *Malassezia* whose abundance ratios were higher were compared between the healthy group and the disease group.
Figure 10B:
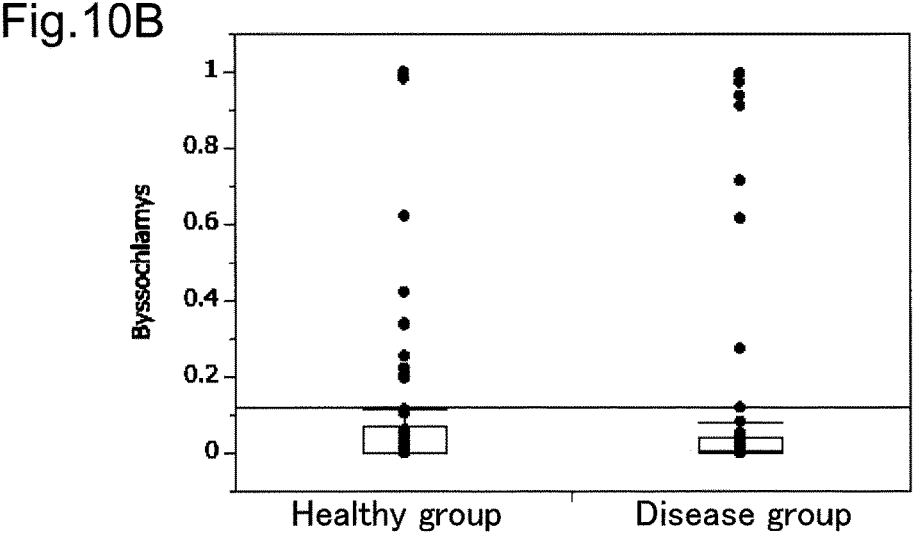
FIG. 10B is a box-and-whisker plot showing a result of further detailed examination of a difference between the bacterial composition of the microbiota of the conjunctiva from the healthy group and that from the disease group, and is showing a result in which abundance ratios of *Byssochlamys* genus whose abundance ratios were higher were compared between the healthy group and the disease group.
Figure 10C:
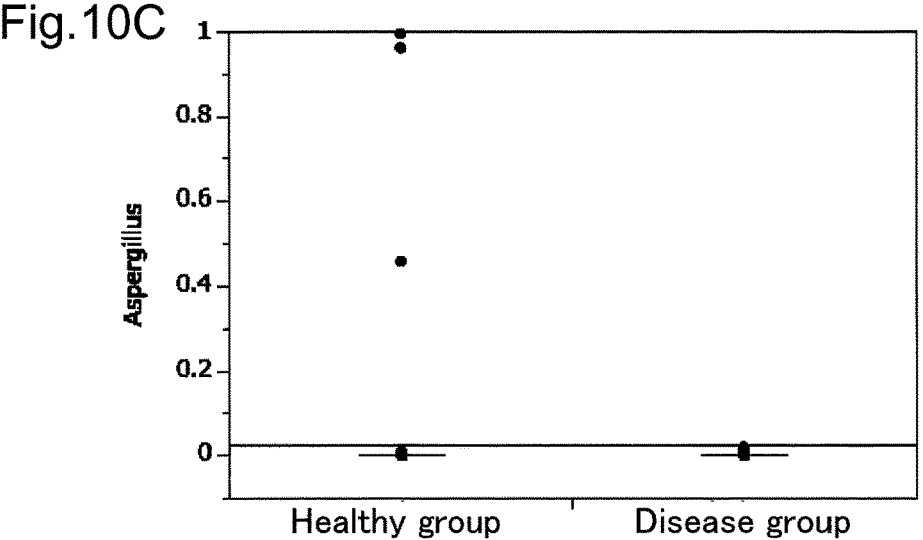
FIG. 10C is a box-and-whisker plot showing a result of further detailed examination of a difference between the bacterial composition of the microbiota of the conjunctiva from the healthy group and that from the disease group, and is showing a result in which abundance ratios of *Aspergillus* genus whose abundance ratios were higher were compared between the healthy group and the disease group.

Fungal compositions of specimens sampled from human ocular surface tissues of the healthy group and of the disease group were compared at a genus level. The results are shown in FIGS. 9, 10A to 10C. In FIG. 9, main fungi constituting microbial layers of the healthy group and of the disease group are indicated, and their relative abundance ratios are shown in graphs. FIGS. 10A to 10C show the results of comparison of the abundance ratios of 3 fungi of *Malassezia* genus, *Byssochlamys* genus, and *Aspergillus* genus, which are ranked higher in abundance ratio, in the healthy group and the disease group. As a result, in any of the identified fungal species, no significant change in the abundance ratios was confirmed between the disease group and the healthy group. Thus, no association was confirmed between conjunctival MALT lymphoma and the fungal composition in microbiota structure, and this strongly supports the results of Examples 1 and 2 in which specific bacterial species, including *Delftia* genus bacteria, *Bacteroides* genus bacteria, and *Clostridium* genus bacteria play an important role in the pathophysiology of conjunctival MALT lymphoma.

[Example 4] Change in Microbiota Due to Age

In this example, a relationship between a change in the microbiota of ocular surface tissues and age was examined. Specifically, a microbial community structure contained in specimens sampled from human ocular surface tissues was analyzed by 16S rRNA gene, and a correlative relationship between the microbial community structure and age was verified.
(Method)

In this example, analysis of microbiotas of ocular surface tissues of 38 healthy persons (78 eyes) aged 21 to 83 years was performed by (sample collection and DNA isolation), and (16S rRNA sequencing and data processing) and (statistical analysis) in the same manner as in Example 1. The breakdown of healthy subjects was 18 males and 21 females, mean age 53.0±19.8 years, and there were no history of ocular diseases, no wearing of contact lenses, and no history of ocular trauma.
(Result)

Figure 11:
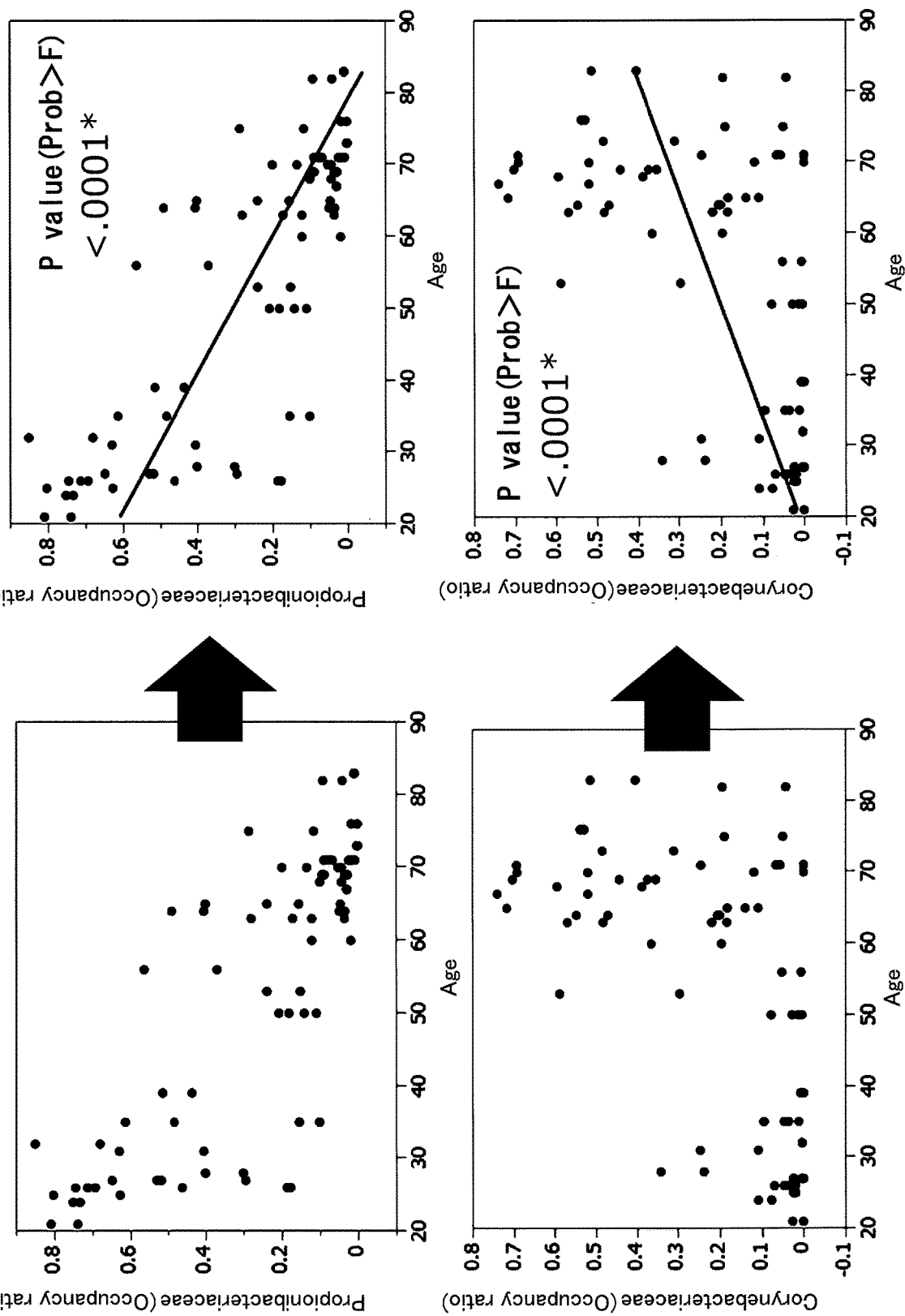
FIG. 11 is graphs showing changes with age in occupancy ratio of Propionibacteriaceae family bacteria and that of Corynebacteriaceae family bacteria in a conjunctiva.
Figure 12:
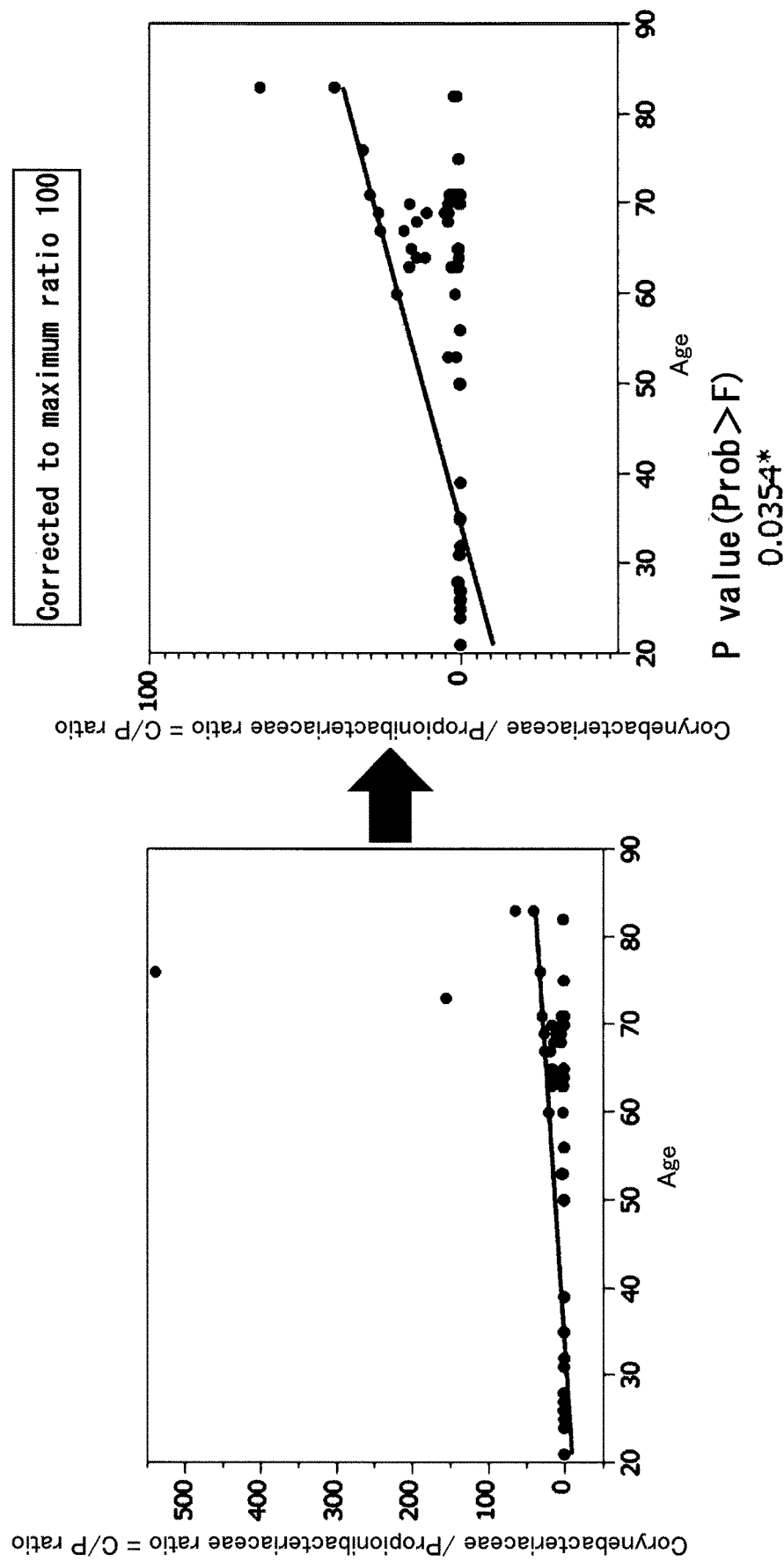
FIG. 12 is graphs showing changes with age in ratio (C/P) of Corynebacteriaceae family bacteria/Propionibacteriaceae family bacteria.
Figure 13:
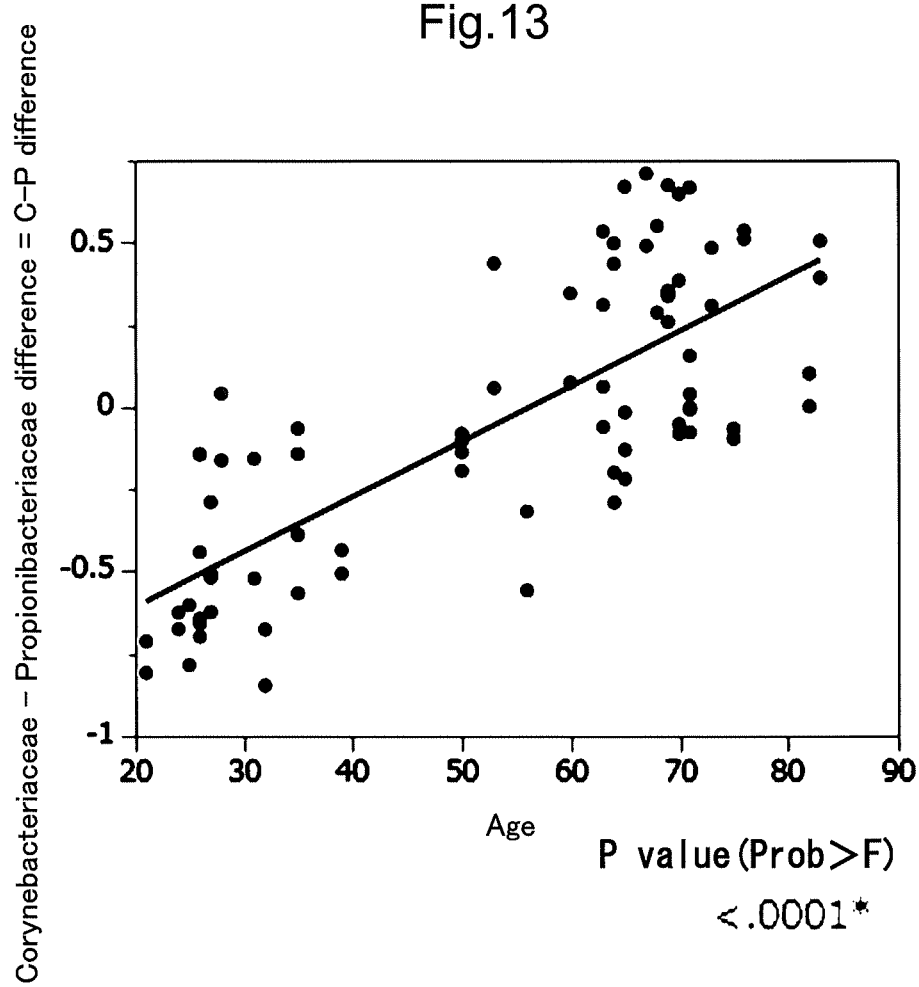
FIG. 13 is a graph showing changes with age in difference (C−P) of Corynebacteriaceae family bacteria-Propionibacteriaceae family bacteria.

Bacterial compositions of the conjunctival microbiota from healthy persons of each age were verified. The results are shown in FIG. 11 to FIG. 13. As a result, it was confirmed that the bacterial composition of the microbiota of the conjunctiva derived from healthy persons of each age fluctuates with aging, and that with the aging, Propionibacteriaceae family bacteria decrease, while Corynebacteriaceae family bacteria increase. FIG. 11 is graphs showing changes with age in occupancy ratios of Propionibacteriaceae family bacteria and of Corynebacteriaceae family bacteria in the conjunctiva. FIG. 12 is graphs showing changes with age in the ratios (C/P) of Corynebacteriaceae family bacteria/Propionibacteriaceae family bacteria. FIG. 13 is a graph showing a change with age in a difference (C−P) of Corynebacteriaceae family bacteria-Propionibacteriaceae family bacteria. From all the results, it can be understood that significant correlative relationships with age changes were observed, and that the abundance ratio of Corynebacteriaceae family bacteria is higher than that of Propionibacteriaceae family bacteria around 60 years of age.

Figure 14:
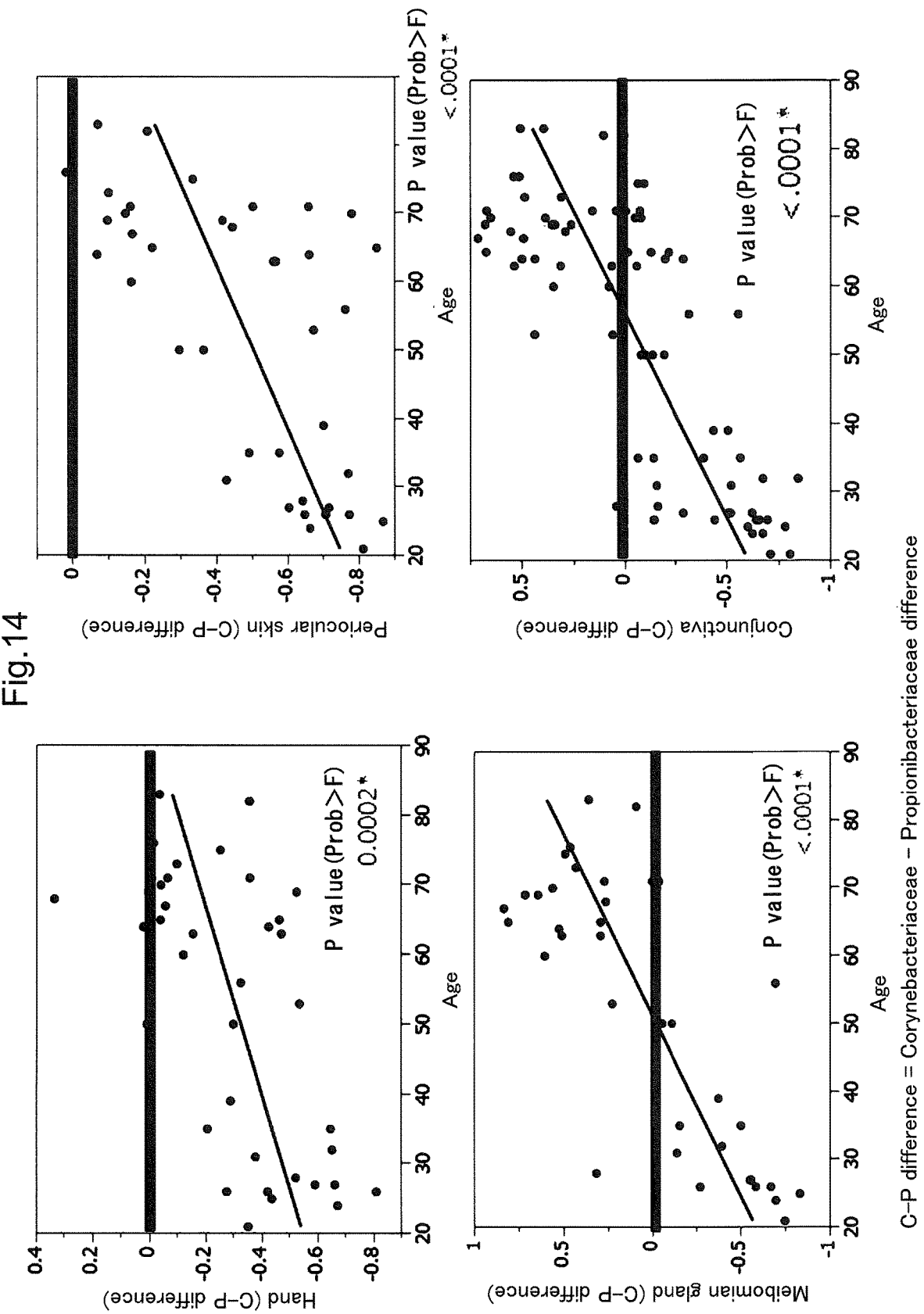
FIG. 14 is a graph showing changes with age in difference (C−P) of Corynebacteriaceae family bacteria-Propionibacteriaceae family bacteria at 4 sites (conjunctiva, meibomian gland, periocular skin, and hand) from which specimens were sampled.

Furthermore, changes with age in a difference (C−P) of Corynebacteriaceae family bacteria-Propionibacteriaceae family bacteria were verified at 4 sites: conjunctiva, meibomian gland, hand, and periocular skin. The results are shown in FIG. 14, and FIG. 14 is graphs showing changes with age in the difference (C–P) of Corynebacteriaceae family bacteria-Propionibacteriaceae family bacteria in the conjunctiva, meibomian gland, hand, and periocular skin. As a result, changes with age in the difference (C–P) of Corynebacteriaceae family bacteria-Propionibacteriaceae family bacteria were observed at all sites, and the abundance of Corynebacteriaceae family bacteria increased with aging. However, only ocular surface tissues of the conjunctival and meibomian gland showed that the abundance of Corynebacteriaceae family bacteria was higher than that of Propionibacteriaceae family bacteria. From this, it can be understood that the aging state of the subject can be detected by the ocular surface tissue and the difference appears remarkably, which enables to detect the aging state of the subject with high reliability. Similarly, for fungi in the microbial community structure, a correlation relationship with age was also analyzed, but no significant change in specific fungal species was confirmed. This also strongly supports the above result that Corynebacteriaceae family bacteria and Propionibacteriaceae family bacteria are specifically associated with the aging state and play a role as an aging biomarker.

INDUSTRIAL APPLICABILITY

The present invention can be used for detection of a pathological state of conjunctival disease, and all technical fields that require detection of an aging state, for example, onset of conjunctival disease, onset risk, and prediction of the degree of progression, investigation of the cause of conjunctival disease, confirming the therapeutic effect of conjunctival diseases by pharmaceuticals and the like, detecting physiological and pathological aging conditions, and the like, and can be used particularly in the medical field, the pharmaceutical field, and the like.

What is claimed is:

1. A method of detecting a conjunctival mucosa-associated lymphoid tissue lymphoma of a subject using microbiota of ocular surface tissue specimens from a healthy person and the subject, the method comprising:
   (i) obtaining a first ocular surface tissue specimen from the healthy person and a second ocular surface tissue specimen from the subject,
   (ii) performing a metagenomic analysis using a next-generation sequencer, on the first ocular surface tissue specimen and the second ocular surface tissue specimen so as to obtain sequence information of 16S rRNA genes of each bacterial species in each of the first ocular surface tissue specimen and the second ocular surface tissue specimen,
   (iii) determining an abundance of a 16S rRNA gene of each of the bacterial species including at least one Delftia bacterial species in each of the first ocular surface tissue specimen and the second ocular surface tissue specimen by merging the sequence information of the 16S rRNA genes and taxonomically classifying merged sequences of each specimen so as to determine the bacterial species and the amount of each bacterial species contained in the first ocular surface tissue specimen and the second ocular surface tissue specimen; and calculating (a) an abundance ratio of each of the Delftia bacterial species present in the first ocular surface tissue specimen relative to all bacterial species present in the first ocular surface tissue specimen and (b) an abundance ratio of each of the Delftia bacterial species present in the second ocular surface tissue specimen relative to all bacterial species present in the second ocular surface tissue specimen,
   (iv) comparing a first microbial community structure of a microbiota of the first ocular surface tissue specimen, which is the abundance ratio of the at least one Delftia bacterial species in the first ocular surface tissue specimen, with a second microbial community structure of a microbiota of the second ocular surface tissue specimen, which is the abundance ratio of the at least one Delftia bacterial species in the second ocular surface tissue specimen, and
   (v) determining that the second ocular surface tissue specimen has an indication of the conjunctival mucosa-associated lymphoid tissue lymphoma when the abundance ratio of the at least one Delftia bacterial species in the second microbial community structure is significantly higher than the abundance ratio of the at least one Delftia bacterial species in the first microbial community structure.

2. The method according to claim 1, wherein the metagenomic analysis includes amplifying a part of the 16S rRNA genes of all bacterial species present in each of the first ocular surface tissue specimen and the second ocular surface tissue specimen to produce amplicons, sequencing the amplicons to obtain sequence reads, merging the sequence reads to obtain merged sequences, trimming the merged sequences to produce processed reads, clustering of the processed reads to obtain taxonomically classified reads.

3. The method according to claim 2, wherein the abundance of the 16S rRNA gene of the at least one Delftia bacterial species is determined based on the abundance of the processed reads that correspond to the 16S IRNA gene of the at least one Delftia bacterial species present in the sequence information of 16S rRNA genes of the all bacterial species.

4. The method according to claim 2, wherein the comparing comprises a linear discriminant analysis effect size analysis of the taxonomically classified reads.

5. The method according to claim 1, wherein the subject on whom the method is practiced is a human who has been identified as having developed conjunctival mucosa-associated lymphoid tissue lymphoma, or as having a risk of developing conjunctival mucosa-associated lymphoid tissue lymphoma.

6. A method of detecting and treating a conjunctival mucosa-associated lymphoid tissue lymphoma of a subject, wherein the method comprises the method according to claim 1, and
   (vi) treating the conjunctival mucosa-associated lymphoid tissue lymphoma on the subject from which the second ocular surface tissue specimen, which has been determined to have an indication of the conjunctival mucosa-associated lymphoid tissue lymphoma, has been obtained.

7. The method according to claim 1, further comprising: measuring a pH of a tear fluid of the subject.

8. The method according to claim 1, further comprising: measuring an IgA concentration in a tear fluid of the subject.

* * * * *